(12) United States Patent
Asano et al.

(10) Patent No.: US 11,504,379 B2
(45) Date of Patent: Nov. 22, 2022

(54) AMIDE COMPOUND, AND PIN1 INHIBITOR, THERAPEUTIC AGENT FOR INFLAMMATORY DISEASES AND THERAPEUTIC AGENT FOR CANCER THAT USE THE SAME

(71) Applicants: Hiroshima University, Higashihiroshima (JP); Tokyo University of Pharmacy & Life Sciences, Hachioji (JP); The University of Tokyo, Tokyo (JP)

(72) Inventors: Tomoichiro Asano, Hiroshima (JP); Yusuke Nakatsu, Hiroshima (JP); Hisanaka Ito, Hachioji (JP); Takayoshi Okabe, Tokyo (JP)

(73) Assignees: Hiroshima University, Hiroshima (JP); Tokyo University of Pharmacy & Life Sciences, Tokyo (JP); The University of Tokyo, Tokyo (JP)

( * ) Notice: Subject to any disclaimer, the term of this patent is extended or adjusted under 35 U.S.C. 154(b) by 44 days.

(21) Appl. No.: 16/636,746

(22) PCT Filed: Aug. 6, 2018

(86) PCT No.: PCT/JP2018/029495
§ 371 (c)(1),
(2) Date: Feb. 5, 2020

(87) PCT Pub. No.: WO2019/031470
PCT Pub. Date: Feb. 14, 2019

(65) Prior Publication Data
US 2020/0383987 A1 Dec. 10, 2020

(30) Foreign Application Priority Data
Aug. 7, 2017 (JP) .............................. JP2017-152806

(51) Int. Cl.
| | |
|---|---|
| *C07C 275/36* | (2006.01) |
| *C07C 275/28* | (2006.01) |
| *C07C 275/38* | (2006.01) |
| *C07C 233/46* | (2006.01) |
| *C07C 233/63* | (2006.01) |
| *C07C 233/51* | (2006.01) |
| *C07C 233/87* | (2006.01) |
| *C07C 271/22* | (2006.01) |

(Continued)

(52) U.S. Cl.
CPC .......... *A61K 31/538* (2013.01); *A61K 31/198* (2013.01); *A61K 31/216* (2013.01); *A61K 31/404* (2013.01); *A61K 31/473* (2013.01); *A61K 45/06* (2013.01); *A61P 35/00* (2018.01); *C07C 233/46* (2013.01); *C07C 233/51* (2013.01); *C07C 275/28* (2013.01); *C07D 209/88* (2013.01); *C07D 215/02* (2013.01); *C07D 295/195* (2013.01)

(58) Field of Classification Search
CPC . C07C 2601/18; C07C 275/36; C07C 275/28; C07C 275/38; C07C 233/46; C07C 233/63; C07C 233/51; C07C 233/87; C07C 271/22; C07C 235/40; C07D 209/88; C07D 209/82; C07D 215/02; C07D 295/195; C07D 233/24; C07D 265/38; A61P 3/04; A61P 29/00; A61P 35/00; A61K 45/06; A61K 31/216
See application file for complete search history.

(56) References Cited

U.S. PATENT DOCUMENTS

| | | |
|---|---|---|
| 5,378,690 A | 1/1995 | Morisawa et al. |
| 5,514,683 A | 5/1996 | Kalindjian et al. |

(Continued)

FOREIGN PATENT DOCUMENTS

| | | |
|---|---|---|
| CN | 101928329 | 7/2013 |
| CN | 101638414 | 1/2014 |

(Continued)

OTHER PUBLICATIONS

RN1829120-71-9, registry database compound, 2015.*

(Continued)

*Primary Examiner* — Sun Jae Yoo
(74) *Attorney, Agent, or Firm* — Jeffrey I. Auerbach; Auerbach, LLC

(57) ABSTRACT

The purpose of the invention is to develop, as drug-candidate compounds, a group of novel compounds having the activity of inhibiting functions of Pin1. The invention provides: a compound represented by formula (I) or a salt thereof; and a Pin1 inhibitor, a pharmaceutical composition, a therapeutic or prophylactic agent for inflammatory diseases, a therapeutic or prophylactic agent for cancer, and a therapeutic or prophylactic agent for adiposity that use said compound/salt.

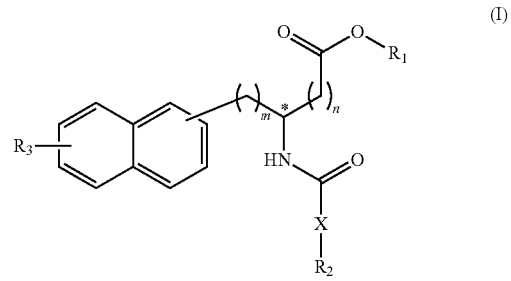

22 Claims, 5 Drawing Sheets

(51) Int. Cl.
| | |
|---|---|
| *C07C 235/40* | (2006.01) |
| *C07D 209/88* | (2006.01) |
| *C07D 209/82* | (2006.01) |
| *C07D 215/02* | (2006.01) |
| *C07D 295/195* | (2006.01) |
| *C07D 233/24* | (2006.01) |
| *C07D 265/38* | (2006.01) |
| *A61P 3/04* | (2006.01) |
| *A61P 29/00* | (2006.01) |
| *A61P 35/00* | (2006.01) |
| *A61K 45/06* | (2006.01) |
| *A61K 31/216* | (2006.01) |
| *A61K 31/473* | (2006.01) |
| *A61K 31/198* | (2006.01) |
| *A61K 31/538* | (2006.01) |
| *A61K 31/404* | (2006.01) |

(56) References Cited

U.S. PATENT DOCUMENTS

| | | | |
|---|---|---|---|
| 2006/0079454 A1 | 4/2006 | Reches et al. | |
| 2012/0135921 A1 | 5/2012 | Li et al. | |
| 2020/0383989 A1* | 12/2020 | Asano | A61K 31/415 |

FOREIGN PATENT DOCUMENTS

| | | |
|---|---|---|
| EP | 0274259 | 2/1994 |
| EP | 0626942 | 4/1997 |
| EP | 2444411 | 4/2012 |
| EP | 1781310 | 10/2015 |
| JP | 1-199994 | 8/1989 |
| JP | 7-504184 | 5/1995 |
| JP | 10-7540 | 1/1998 |
| JP | 2012-530085 | 11/2012 |
| KR | 10-1993-0000063 | 1/1993 |
| WO | WO 1993/016982 | 9/1993 |
| WO | WO 2006/013552 | 2/2006 |
| WO | WO 2010/012222 | 2/2010 |
| WO | WO 2010/145376 | 12/2010 |

OTHER PUBLICATIONS

CancerPrevention, 2022, https://www.cancerresearchuk.org/about-cancer/causes-of-cancer/can-cancer-be-prevented-0.*
InflammatoryBowelDisease, 2022, https://www.cdc.gov/dotw/ibd/index.html.*
ObesityPrevention, 2022, file:///C:/Users/sloewe/Documents/e-Red%20Folder/16636746/ObesityPrevention.pdf.*
Suzuki et al., PLOS One, 2016, 11(12), 4 pages.*
International Search Report PCT/JP2018/029495 (WO 2019/031470) (dated 2018) (3 pages).
Registry (STN) (online), Apr. 14, 2011, CAS: 1279815-69-8.
Registry (STN) (online), Dec. 14, 2015, CAS: 1829120-71-9.
Registry (STN) (online), Dec. 14, 2015, CAS: 1829181-88-5.
Written Opinion of the International Searching Authority PCT/JP2018/029495 (WO 2019/031470) (6 pages).

* cited by examiner (A)

(B)

(C)

(A)

Normal diet (B)

HFDT (C)

HFDT + H-163

(A) Normal diet (B) MCDD (C) MCDD + H-163

(A)

(B)

AMIDE COMPOUND, AND PIN1 INHIBITOR, THERAPEUTIC AGENT FOR INFLAMMATORY DISEASES AND THERAPEUTIC AGENT FOR CANCER THAT USE THE SAME

CROSS-REFERENCE TO RELATED APPLICATIONS

This application is a § 371 Application of PCT/JP2018/029495 (filed on Aug. 6, 2018), which application claims priority to Japanese Patent Application 2017-152806 (filed on Aug. 7, 2017), each of which applications is incorporated herein by reference in its entirety and to which priority is claimed.

TECHNICAL FIELD

The present invention relates to new low-molecular-weight organic amide compounds, and further relates to Pin1 inhibitors, pharmaceutical compositions, therapeutic or prophylactic agents for inflammatory diseases including non-alcoholic steatohepatitis (NASH), inflammatory bowel disease, and pulmonary fibrosis, for cancer, and for obesity, which are prepared using the compounds.

BACKGROUND ART

Pin1 is a kind of peptidyl-prolyl cis-trans isomerase (PPIase) that catalyzes cis/trans isomerization of proline residues in proteins, and is characterized in that the enzyme specifically acts on proline residues immediately preceded by phosphorylated serine or threonine to change the conformation of those proline residues. Accordingly, Pin1 is a molecule that couples phosphorylation of a protein to conformational change of the protein, and is considered to play an important role in intracellular signal transduction. In respect of Pin1, it is reported that Pin1 knockout mice manifest Alzheimer's-like pathology (Non-Patent Document 1), and that Pin1 inhibitors have ability to inhibit cancer cell growth (Non-Patent Documents 2 and 3).

Additionally, the inventors have previously reported that Pin1, a kind of cis-trans isomerase, associates with IRS-1, a protein playing a central role in insulin signaling, and enhances insulin signaling (Non-Patent Document 4).

As compounds that inhibit Pint, a phenylalaninol-phosphate derivative, an indole- or benzimidazole-alanine derivative, a fredericamycin A compound, a phenyl-imidazole derivative, a naphthyl-substituted amino acid derivative, a glutamate or aspartate derivative, and the like have been reported (Patent Documents 1 to 4 and Non-Patent Documents 2, 3, 5, and 6).

The inventors previously found that use of Juglone, which is a compound known as a Pin1 inhibitor and having the following structure, and

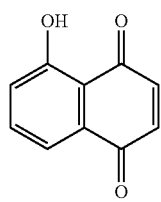

similarly use of (R)-2-(5-(4-methoxyphenyl)-2-methyl-furan-3-carboxamido)-3-(naphthalene-6-yl)propanoic acid (hereinafter referred to as C1), which is a compound known as a Pin1 inhibitor and having the following structure,

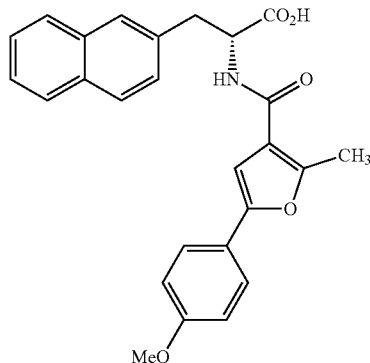 [SMILES: COc1ccc(-c2cc(C(=O)N[C@H](Cc3ccc4ccccc4c3)C(=O)O)c(C)o2)cc1]

resulted in prevention of colitis development in mice with induction of colitis and with oral administration of either of these Pin1 inhibitors (Non-Patent Document 7).

PRIOR ART REFERENCES

Patent Documents

Patent Document 1: WO 2004/087720
Patent Document 2: WO 2006/040646
Patent Document 3: WO 2005/007123
Patent Document 4: WO 2002/060436

Non-Patent Documents

Non-Patent Document 1: Yih-Cherng Liou, and 11 other authors, Nature, Published: Jul. 31, 2003, Vol. 424, pp. 556-561.
Non-Patent Document 2: Andrew Potter, and 16 other authors, Bioorganic & Medicinal Chemistry Letters (Bioorg. Med. Chem. Lett.), Published: Nov. 15, 2010 (Epub: Sep. 17, 2010), Vol. 20, No. 22, pp. 6483-6488.
Non-Patent Document 3: Andrew Potter, and 14 other authors, Bioorganic & Medicinal Chemistry Letters (Bioorg. Med. Chem. Lett.), Published: Jan. 15, 2010 (Epub: Nov. 22, 2009), Vol. 20, No. 2, pp. 586-590.
Non-Patent Document 4: Yusuke Nakatsu, Tomoichiro Asano, and 21 other authors, The Journal of Biological Chemistry (J. Biol. Chem.), Published: Jun. 10, 2011 (Epub: Mar. 17, 2011), Vol. 286, No. 23, pp. 20812-20822.
Non-Patent Document 5: Liming Dong, and 11 other authors, Bioorganic & Medicinal Chemistry Letters (Bioorg. Med. Chem. Lett.), Published: Apr. 1, 2010 (Epub: Feb. 14, 2010), Vol. 20, No. 7, pp. 2210-2214.
Non-Patent Document 6: Hidehiko Nakagawa, and 6 other authors, Bioorganic & Medicinal Chemistry Letters (Bioorg. Med. Chem. Lett.), Published: Dec. 1, 2015 (Epub: Oct. 22, 2015), Vol. 25, pp. 5619-5624.
Non-Patent Document 7: Tomoichiro Asano, "Novel treatment of inflammatory bowel diseases by Pin1 inhibitors", presentation for the DSANJ Biz Meeting Categorized by Target Diseases (gastrointestinal diseases) sponsored by the Osaka Chamber of Commerce and Industry, Published: Jan. 30, 2015.

DISCLOSURE OF THE INVENTION

Problems to be Solved by the Invention

In view of the current conditions as described above, an object of the present invention is to develop a group of new compounds with inhibitory activity against the function of Pin1 as candidate compounds for drugs.

Means for Solving the Problems

The inventors intensively studied to solve the above-described problem, and consequently developed a group of new compounds by synthesizing many amide compounds, each having a naphthyl group attached to two or more rings through carbon or amide bonding, and found that these new compounds have a potential to be therapeutic agents for diseases, such as non-alcoholic steatohepatitis and cancer, as well as have an inhibitory activity against the function of Pin1, and finally completed the present invention.

That is, the present invention provides the following first invention relating to new compounds or salts thereof, the following second invention relating to Pin1 inhibitors, the following third invention relating to pharmaceutical compositions, the following fourth invention relating to therapeutic or prophylactic agents for inflammatory diseases associated with fibrosis including non-alcoholic steatohepatitis, inflammatory bowel disease, and pulmonary fibrosis, the following fifth invention relating to therapeutic or prophylactic agents for cancer, and the following sixth invention relating to therapeutic or prophylactic agents for obesity.

The first invention provides compounds represented by the following Formula (I), or salts thereof:

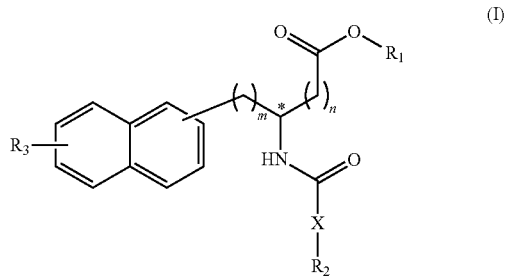

(I)

(wherein m represents an integer of 0 to 2, and n represents an integer of 0 to 1, provided that $0 \leq m+n \leq 2$;

$R_1$ represents a hydrogen atom, an optionally substituted hydrocarbon group, an optionally substituted heterocyclic group, or an optionally substituted amino group;

$R_2$ represents an optionally substituted aryl group containing a condensed ring system with three or more rings, a substituted naphthyl group, or a group represented by the following Formula (II), (III), (IV), or (V):

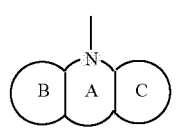

(II)

(wherein a ring A represents an optionally substituted monocyclic heterocyclic group, and rings B and C independently represent an optionally substituted monocyclic or polycyclic aryl or heterocyclic group, and the rings A, B, and C together form a condensed ring system)

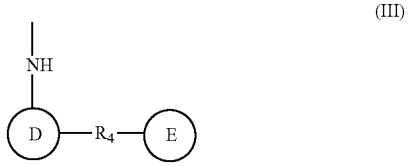

(III)

(wherein rings D and E independently represent an optionally substituted monocyclic or polycyclic aryl or heterocyclic group, and $R_4$ represents a divalent oxy or carbonyl group)

(IV)

(wherein rings D and E independently represent an optionally substituted monocyclic or polycyclic aryl or heterocyclic group)

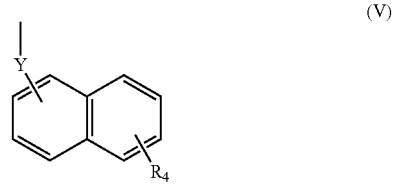

(V)

(wherein $R_4$ represents 0 to 7 identical or different substituents attached to the naphthyl group, and Y represents an —NH— group or an alkylene group containing one or two carbon atoms);

$R_3$ represents 0 to 7 identical or different substituents attached to the naphthyl group; and X represents a single bond, —$CH_2$— group, or —NH— group).

In the compounds or salts thereof according to the first invention, the $R_2$ is preferably a group represented by the following Formula (II):

(II)

(wherein a ring A represents an optionally substituted monocyclic heterocyclic group, and rings B and C independently represent an optionally substituted monocyclic or polycyclic aryl or heterocyclic group, and the rings A, B, and C together form a condensed ring system).

In any aforementioned compound or a salt thereof, said m and n are preferably 1 and 0, respectively.

In any aforementioned compound or a salt thereof, the $R_1$ preferably represents a hydrogen atom.

In any aforementioned compound or a salt thereof, the X preferably represents a single bond.

The second invention provides Pin1 inhibitors comprising any aforementioned compound or a salt thereof.

The third invention provides pharmaceutical compositions comprising any aforementioned compound or a pharmaceutically acceptable salt thereof and a pharmaceutically acceptable carrier.

The fourth invention provides therapeutic or prophylactic agents for inflammatory diseases associated with fibrosis, which comprise a compound represented by following Formula (I) or a pharmaceutically acceptable salt thereof as an active ingredient:

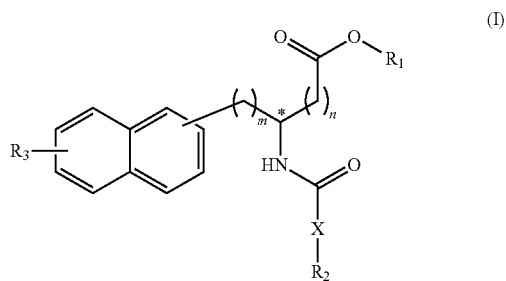

(I)

(wherein m represents an integer of 0 to 2, and n represents an integer of 0 to 1, provided that 0≤m+n≤2;

$R_1$ represents a hydrogen atom, an optionally substituted hydrocarbon group, an optionally substituted heterocyclic group, or an optionally substituted amino group;

$R_2$ represents an optionally substituted aryl group containing a condensed ring system with three or more rings, a substituted naphthyl group, or a group represented by the following Formula (II), (III), (IV), or (V):

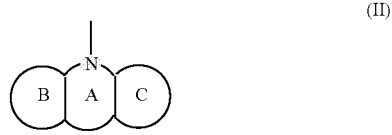

(II)

(wherein a ring A represents an optionally substituted monocyclic heterocyclic group, and rings B and C independently represent an optionally substituted monocyclic or polycyclic aryl or heterocyclic group, and the rings A, B, and C together form a condensed ring system)

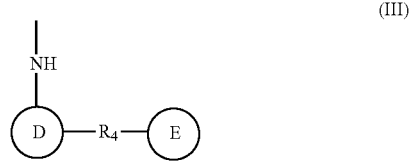

(III)

(wherein rings D and E independently represent an optionally substituted monocyclic or polycyclic aryl or heterocyclic group, and $R_4$ represents a divalent oxy or carbonyl group)

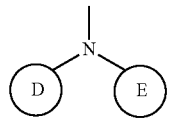

(IV)

(wherein rings D and E independently represent an optionally substituted monocyclic or polycyclic aryl or heterocyclic group)

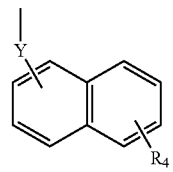

(V)

(wherein $R_4$ represents 0 to 7 identical or different substituents attached to the naphthyl group, and Y represents a —NH— group or an alkylene group containing one or two carbon atoms);

$R_3$ represents 0 to 7 identical or different substituents attached to the naphthyl group; and X represents a single bond, —$CH_2$— group, or —NH— group).

In respect of the therapeutic or prophylactic agents for inflammatory diseases associated with fibrosis according to the fourth invention, the inflammatory diseases associated with fibrosis are non-alcoholic steatohepatitis, inflammatory bowel disease, and pulmonary fibrosis.

In any aforementioned therapeutic or prophylactic agent for an inflammatory disease associated with fibrosis, the $R_2$ is preferably a group represented by the following Formula (II):

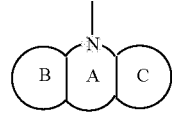

(II)

(wherein a ring A represents an optionally substituted monocyclic heterocyclic group, and rings B and C independently represent an optionally substituted monocyclic or polycyclic aryl or heterocyclic group, and the rings A, B, and C together form a condensed ring system).

In any aforementioned therapeutic or prophylactic agent for an inflammatory disease associated with fibrosis, said m and n are preferably 1 and 0, respectively.

In any aforementioned therapeutic or prophylactic agent for an inflammatory disease associated with fibrosis, the $R_1$ preferably represents a hydrogen atom.

In any aforementioned therapeutic or prophylactic agent for an inflammatory disease associated with fibrosis, the X preferably represents a single bond.

Any aforementioned therapeutic or prophylactic agent for an inflammatory disease associated with fibrosis may further comprise active ingredients in at least one or more drugs selected from the group of other therapeutic or prophylactic agents for the inflammatory disease associated with fibrosis.

Moreover, any aforementioned therapeutic or prophylactic agent for an inflammatory disease associated with fibrosis may be used in combination with at least one or more drugs selected from the group of other therapeutic or prophylactic agents for the inflammatory disease associated with fibrosis.

The fourth invention provides any aforementioned compound or a pharmaceutically acceptable salt thereof for use as a therapeutic or prophylactic agent for an inflammatory disease associated with fibrosis.

The fourth invention also provides use of any aforementioned compound or a pharmaceutically acceptable salt thereof for the manufacture of a medicament for the treatment or prevention of an inflammatory disease associated with fibrosis.

Moreover, the fourth invention also provides a method of treating or preventing an inflammatory disease associated with fibrosis by administering any aforementioned compound or a pharmaceutically acceptable salt thereof to a patient.

The fifth invention provides therapeutic or prophylactic agents for cancer, which comprise a compound represented by following Formula (I) or a pharmaceutically acceptable salt thereof as an active ingredient:

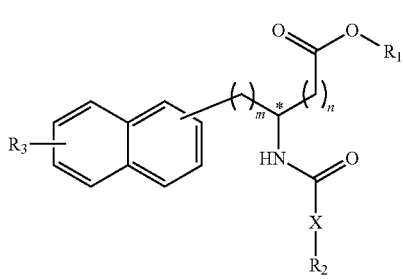

(I)

(wherein m represents an integer of 0 to 2, and n represents an integer of 0 to 1, provided that $0 \leq m+n \leq 2$;

$R_1$ represents a hydrogen atom, an optionally substituted hydrocarbon group, an optionally substituted heterocyclic group, or an optionally substituted amino group;

$R_2$ represents an optionally substituted aryl group containing a condensed ring system with three or more rings, a substituted naphthyl group, or a group represented by the following Formula (II), (III), (IV), or (V):

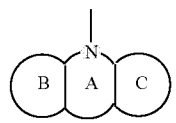

(II)

(wherein a ring A represents an optionally substituted monocyclic heterocyclic group, and rings B and C independently represent an optionally substituted monocyclic or polycyclic aryl or heterocyclic group, and the rings A, B, and C together form a condensed ring system)

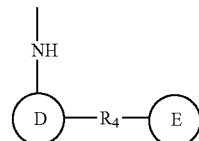

(III)

(wherein rings D and E independently represent an optionally substituted monocyclic or polycyclic aryl or heterocyclic group, and $R_4$ represents a divalent oxy or carbonyl group)

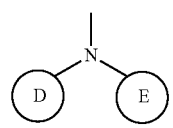

(IV)

(wherein rings D and E independently represent an optionally substituted monocyclic or polycyclic aryl or heterocyclic group)

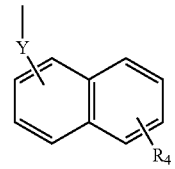

(V)

(wherein $R_4$ represents 0 to 7 identical or different substituents attached to the naphthyl group, and Y represents a —NH— group or an alkylene group containing one or two carbon atoms);

$R_3$ represents 0 to 7 identical or different substituents attached to the naphthyl group; and X represents a single bond, —$CH_2$— group, or —NH— group).

The therapeutic or prophylactic agents for cancer according to the fifth invention can be suitably used when the cancer is colon cancer or prostate cancer.

In any aforementioned therapeutic or prophylactic agent for cancer, the $R_2$ is preferably a group represented by the following Formula (II):

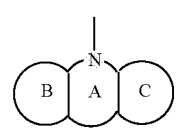

(II)

(wherein a ring A represents an optionally substituted monocyclic heterocyclic group, and rings B and C independently represent an optionally substituted monocyclic or polycyclic aryl or heterocyclic group, and the rings A, B, and C together form a condensed ring system).

In any aforementioned therapeutic or prophylactic agent for cancer, said m and n are preferably 1 and 0, respectively.

In any aforementioned therapeutic or prophylactic agent for cancer, the $R_1$ preferably represents a hydrogen atom.

In any aforementioned therapeutic or prophylactic agent for cancer, the X preferably represents a single bond.

Any aforementioned therapeutic or prophylactic agent for cancer may further comprise active ingredients in at least one or more drugs selected from the group of other therapeutic or prophylactic agents for cancer.

Moreover, any aforementioned therapeutic or prophylactic agent for cancer may be used in combination with at least one or more drugs selected from the group of other therapeutic or prophylactic agents for cancer.

The fifth invention provides any aforementioned compound or a pharmaceutically acceptable salt thereof for use as a therapeutic or prophylactic agent for cancer.

The fifth invention also provides use of any aforementioned compound or a pharmaceutically acceptable salt thereof for the manufacture of a medicament for the treatment or prevention of cancer.

Moreover, the fifth invention also provides a method of treating or preventing cancer by administering any aforementioned compound or a pharmaceutically acceptable salt thereof to a patient.

The sixth invention provides therapeutic or prophylactic agents for obesity, which comprise a compound represented by following Formula (I) or a pharmaceutically acceptable salt thereof as an active ingredient:

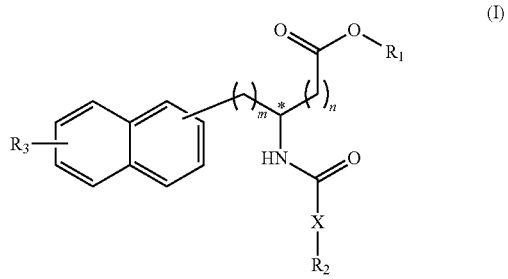
(I)

(wherein m represents an integer of 0 to 2, and n represents an integer of 0 to 1, provided that 0≤m+n≤2;

$R_1$ represents a hydrogen atom, an optionally substituted hydrocarbon group, an optionally substituted heterocyclic group, or an optionally substituted amino group;

$R_2$ represents an optionally substituted aryl group containing a condensed ring system with three or more rings, a substituted naphthyl group, or a group represented by the following Formula (II), (III), (IV), or (V):

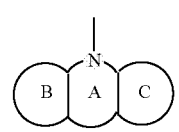
(II)

(wherein a ring A represents an optionally substituted monocyclic heterocyclic group, and rings B and C independently represent an optionally substituted monocyclic or polycyclic aryl or heterocyclic group, and the rings A, B, and C together form a condensed ring system)

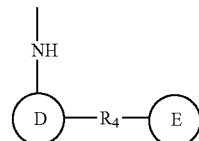
(III)

(wherein rings D and E independently represent an optionally substituted monocyclic or polycyclic aryl or heterocyclic group, and $R_4$ represents a divalent oxy or carbonyl group)

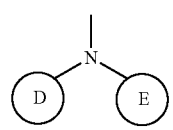
(IV)

(wherein rings D and E independently represent an optionally substituted monocyclic or polycyclic aryl or heterocyclic group)

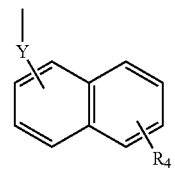
(V)

(wherein $R_4$ represents 0 to 7 identical or different substituents attached to the naphthyl group, and Y represents a —NH— group or an alkylene group containing one or two carbon atoms);

$R_3$ represents 0 to 7 identical or different substituents attached to the naphthyl group; and X represents a single bond, —CH$_2$— group, or —NH— group).

In the therapeutic or prophylactic agents for obesity according to the sixth invention, the $R_2$ is preferably a group represented by the following Formula (II):

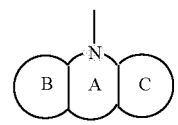
(II)

(wherein a ring A represents an optionally substituted monocyclic heterocyclic group, and rings B and C independently represent an optionally substituted monocyclic or polycyclic aryl or heterocyclic group, and the rings A, B, and C together form a condensed ring system).

In any aforementioned therapeutic or prophylactic agent for obesity, said m and n are preferably 1 and 0, respectively.

In any aforementioned therapeutic or prophylactic agent for obesity, the $R_1$ preferably represents a hydrogen atom.

In any aforementioned therapeutic or prophylactic agent for obesity, the X preferably represents a single bond.

Any aforementioned therapeutic or prophylactic agent for obesity may further comprise active ingredients in at least one or more drugs selected from the group of other therapeutic or prophylactic agents for obesity.

Moreover, any aforementioned therapeutic or prophylactic agent for obesity may be used in combination with at least one or more drugs selected from the group of other therapeutic or prophylactic agents for obesity.

The sixth invention provides any aforementioned compound or a pharmaceutically acceptable salt thereof for use as a therapeutic or prophylactic agent for obesity.

The sixth invention also provides use of any aforementioned compound or a pharmaceutically acceptable salt thereof for the manufacture of a medicament for the treatment or prevention of obesity.

Moreover, the sixth invention also provides a method of treating or preventing obesity by administering any aforementioned compound or a pharmaceutically acceptable salt thereof to a patient.

Effect of the Invention

Any new compound or a salt thereof according to the first invention is a compound with inhibitory activity against the function of Pin1, or a precursor thereof, or becomes a therapeutic or prophylactic agent or a prodrug thereof for, for example, non-alcoholic steatohepatitis or cancer, and therefore can be effectively used for development of a Pin1 inhibitor or a drug used for inflammatory diseases or cancer.

Any Pin1 inhibitor according to the second invention exerts an inhibitory activity against the function of Pin1.

Pharmaceutical compositions according to the third invention have an effect based on inhibition of Pin1 function as a mechanism of action to treat or prevent diseases.

Therapeutic or prophylactic agents for inflammatory diseases associated with fibrosis according to the fourth invention have an effect to alleviate the conditions of inflammatory diseases associated with fibrosis, such as non-alcoholic steatohepatitis, inflammatory bowel disease, and pulmonary fibrosis, or to prevent development of inflammatory diseases associated with fibrosis.

Therapeutic or prophylactic agents for cancer according to the fifth invention have an effect to inhibit cancer growth or an effect to prevent cancer development.

Therapeutic or prophylactic agents for obesity according to the sixth invention have an effect to reduce accumulation of body fat and thereby to treat or prevent obesity.

BRIEF DESCRIPTION OF THE DRAWINGS

FIG. 1 (A) is a graph depicting the result of measurement of mouse liver weight, and FIG. 1 (B) is a graph depicting the result of measurement of blood ALT (GPT) concentration in mice, and FIG. 1 (C) is a graph depicting the result of measurement of fasting blood glucose concentration in mice. In each of FIGS. 1 (A) to (C), graph bars represent the measurement results in control mice, NASH mice, NASH mice treated by intraperitoneal administration of H-163, NASH mice treated by oral administration of H-163, NASH mice treated by intraperitoneal administration of H-144, NASH mice treated by oral administration of H-144, NASH mice treated by intraperitoneal administration of Juglone, and NASH mice treated by oral administration of Juglone, from left to right.

FIG. 2 (A) is a photograph depicting the result of observation of liver tissue from control mice given a normal diet, and FIG. 2 (B) is a photograph depicting the result of observation of liver tissue from NASH mice given a HFDT, and FIG. 2 (C) is a photograph depicting the result of observation of liver tissue from NASH mice given a HFDT and H-163.

FIG. 3 (A) is a photograph depicting the result of observation of liver tissue from control mice given a normal diet, and FIG. 3 (B) is a photograph depicting the result of observation of liver tissue from NASH mice given a MCDD, and FIG. 3 (C) is a photograph depicting the result of observation of liver tissue from NASH mice given a MCDD and H-163.

FIG. 4 (A) illustrates the distribution of tumor volume ratio (%) in the first tumor at 9 weeks after administration of each compound, where the tumor volume at the beginning of the administration is set as 100, and shows the distribution of size change in control mice, mice given H-163, and mice given H-144, from left to right, expressed in box plot. FIG. 4 (B) illustrates the distribution of volume of the second tumor and shows the distribution of tumor volume in control mice, mice given H-163, and mice given H-144, from left to right, expressed in box plot.

DESCRIPTION OF EMBODIMENTS

Figure 1:
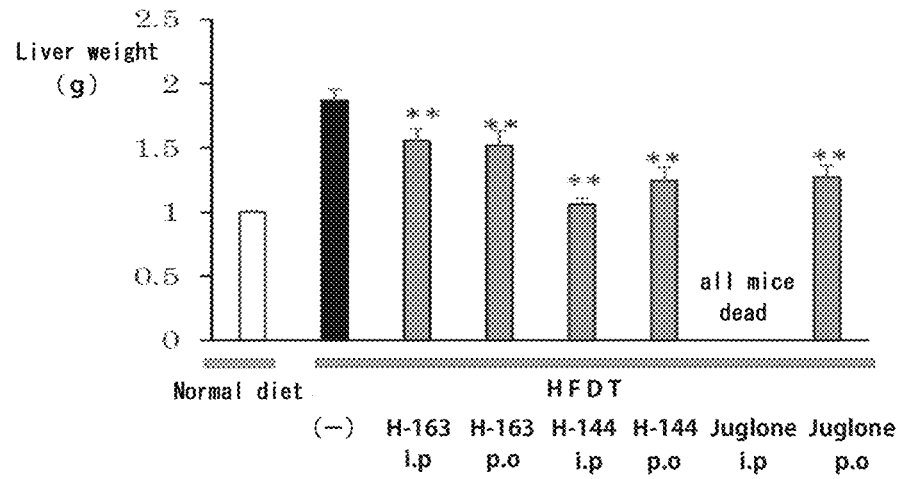
FIG. 1 shows graphs depicting results of measurements of liver weight, blood ALT (GPT) concentration, and fasting blood glucose concentration in mice in a NASH treatment study.
Figure 1:
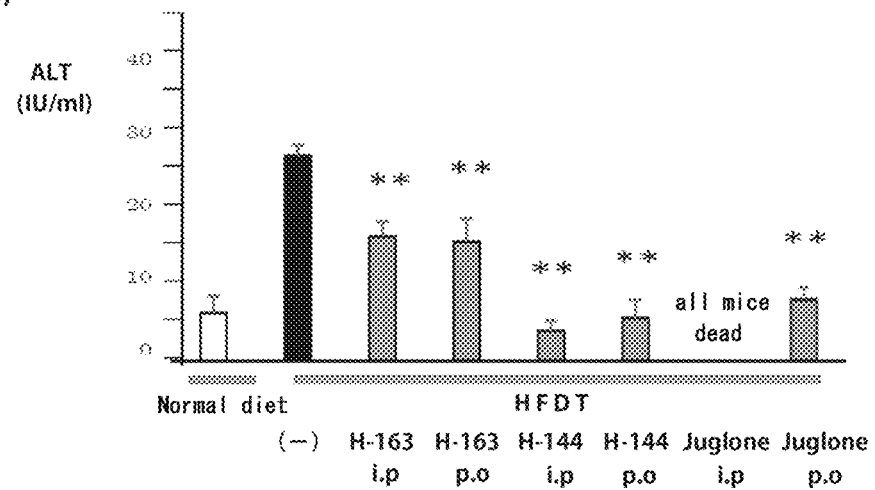
Figure 1:
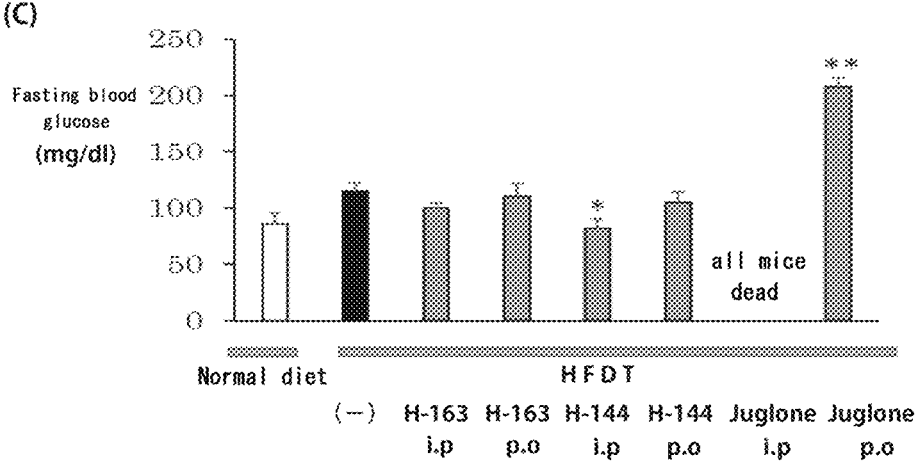

1. Compounds or Salts Thereof
1-1. Structure of Compounds

A compound according to the present invention has a chemical structure represented by the following Formula (I).

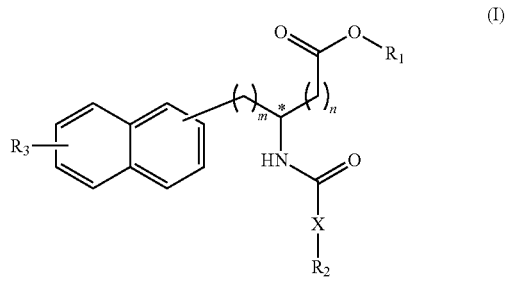

In the Formula (I), m represents an integer of 0 to 2, and n represents an integer of 0 to 1, provided that m and n are integers that satisfy the following relation: $0 \leq m+n \leq 2$. That is, there are five combinations of (m, n): (0, 0), (0, 1), (1, 0), (1, 1), and (2, 0).

The compound according to the present invention comprises a naphthyl moiety and a chain moiety attached to the naphthyl moiety, and can have a structure in which the chain moiety is attached to the naphthyl group at any position. However, the structures of the compound are roughly classified into two types: a structure in which the chain moiety is attached to position 1 of the naphthyl group, and a structure in which the chain moiety is attached to position 2 of the naphthyl group.

The compound according to the present invention can have any of five chemical structures represented by the following Formulae (VI) to (X) and based on the five combinations of (m, n), in cases where the chain moiety is attached to position 2 of the naphthyl group.

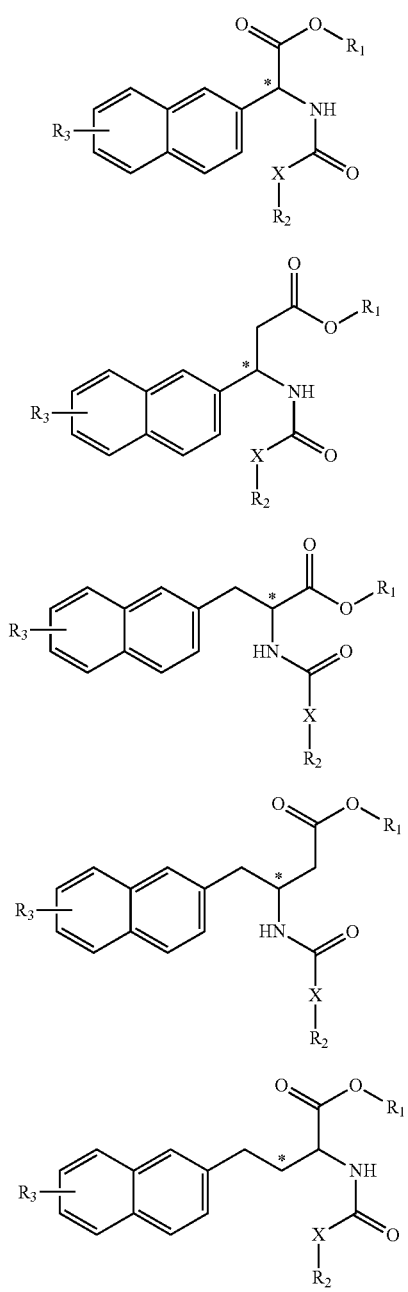

The Formula (VI) represents a variation of the Formula (I), where $m=0$ and $n=0$.

The Formula (VII) represents a variation of the Formula (I), where $m=0$ and $n=1$.

The Formula (VIII) represents a variation of the Formula (I), where $m=1$ and $n=0$.

The Formula (IX) represents a variation of the Formula (I), where $m=1$ and $n=1$.

The Formula (X) represents a variation of the Formula (I), where $m=2$ and $n=0$.

The compound according to the present invention is preferably any of the compounds represented by the Formulae (VI) to (X) in which the chain moiety is attached to position 2 of the naphthyl group, particularly preferably the compound represented by the Formula (VIII) in which $m=1$ and $n=0$.

Similarly, the compound according to the present invention can have any of five chemical structures represented by the following Formulae (XI) to (XV) and based on the five combinations of (m, n), in cases where the chain moiety is attached to position 1 of the naphthyl group.

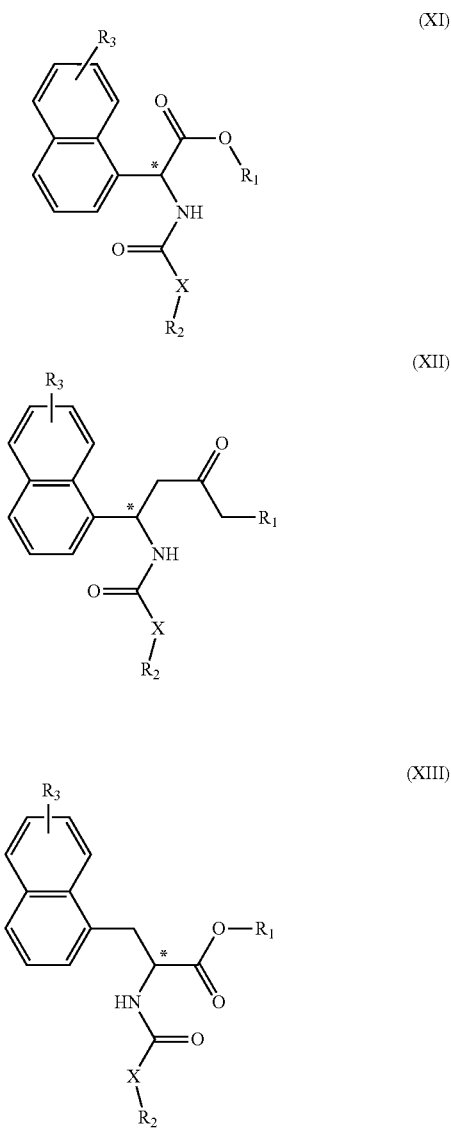

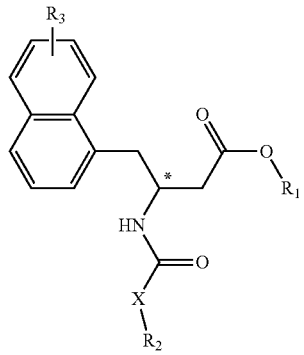

(XIV)

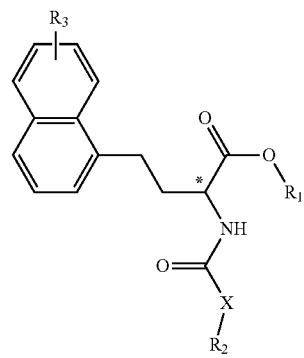

(XV)

In the Formula (I) that represents a compound according to the present invention, $R_1$ represents a hydrogen atom, an optionally substituted hydrocarbon group, an optionally substituted heterocyclic group, or an optionally substituted amino group.

In cases where $R_1$ represents a hydrogen atom to form a carboxyl group, the resultant compound according to the present invention has an inhibitory activity against the function of Pin1. Thus, $R_1$ preferably represents a hydrogen atom.

However, in cases where $R_1$ represents an optionally substituted hydrocarbon group, an optionally substituted heterocyclic group, or an optionally substituted amino group, the $R_1$ moiety in the compound represented by the Formula (I) is attached via an ester bond, and the ester bond can be hydrolyzed to form a carboxyl group. Thus, even if $R_1$ is an optionally substituted hydrocarbon group, an optionally substituted heterocyclic group, or an optionally substituted amino group, the compound according to the present invention can be used as a prodrug.

In the present invention, the "hydrocarbon group" used for, for example, $R_1$ in the Formula (I) means a group derived from a compound composed of carbon and hydrogen atoms. Examples of the hydrocarbon group can include, but are not limited to, aliphatic hydrocarbon, monocyclic saturated hydrocarbon, and aromatic hydrocarbon groups, and preferably contain 1 to 16 carbon atoms. Specific examples of the hydrocarbon group include, but are not limited to, alkyl groups, alkenyl groups, alkynyl groups, cycloalkyl groups, aryl groups, and aralkyl groups.

In this respect, examples of "alkyl group" include methyl group, ethyl group, propyl group, isopropyl group, butyl group, isobutyl group, sec-butyl group, tert-butyl group, pentyl group, and hexyl group. Examples of "alkenyl group" include vinyl group, 1-propenyl group, allyl group, isopropenyl group, butenyl group, and isobutenyl group. Examples of "alkynyl group" include ethynyl group, propargyl group, and 1-propynyl group. Examples of "cycloalkyl group" include cyclopropyl group, cyclobutyl group, cyclopentyl group, and cyclohexyl group. Examples of "aryl group" include phenyl group, indenyl group, naphthyl group, fluorenyl group, anthryl group, biphenylenyl group, phenanthrenyl group, as-indacenyl group, s-indacenyl group, acenaphthylenyl group, phenalenyl group, fluoranthenyl group, pyrenyl group, naphthacenyl group, and hexacenyl group. Examples of "aralkyl group" include benzyl group, styryl group, and phenethyl group.

In the present invention, the "heterocyclic group" used for, for example, $R_1$ in the Formula (I) refers to a group derived from a cyclic compound composed of atoms of carbon and some other elements. As the "heterocyclic group," an aromatic heterocyclic group is preferably used.

In the present invention, the "heterocyclic group" can be, but is not limited to, for example, any of 5- to 14-membered monocyclic to pentacyclic heterocyclic groups each having carbon atoms and further having one to four heteroatoms of one or two elements selected from nitrogen, oxygen, and sulfur. Specific examples of the heterocyclic group can include, but are not limited to, 5-membered cyclic groups each having carbon atoms and further having one to four heteroatoms selected from oxygen, sulfur, and nitrogen, such as 2- or 3-thienyl group, 2- or 3-furyl group, 1-, 2- or 3-pyrrolyl group, 1-, 2- or 3-pyrrolidinyl group, 2-, 4- or 5-oxazolyl group, 3-, 4- or 5-isooxazolyl group, 2-, 4- or 5-thiazolyl group, 3-, 4- or 5-isothiazolyl group, 3-, 4- or 5-pyrazolyl group, 2-, 3- or 4-pyrazolidinyl group, 2-, 4- or 5-imidazolyl group, 1,2,3-triazolyl group, 1,2,4-triazolyl group, and 1H- or 2H-tetrazolyl group. Moreover, specific examples of the heterocyclic group can include 6-membered cyclic groups each having carbon atoms and further having one to four heteroatoms selected from oxygen, sulfur, and nitrogen, such as 2-, 3- or 4-pyridyl group, N-oxide-2-, 3- or 4-pyridyl group, 2-, 4- or 5-pyrimidinyl group, N-oxide-2-, 4- or 5-pyrimidinyl group, thiomorpholinyl group, morpholinyl group, piperidino group, 2-, 3- or 4-piperidyl group, thiopyranyl group, 1,4-oxazinyl group, 1,4-thiazinyl group, 1,3-thiazinyl group, piperazinyl group, triazinyl group, 3- or 4-pyridazinyl group, pyrazinyl group, and N-oxide-3- or 4-pyridazinyl group. Moreover, specific examples of the heterocyclic group can include bicyclic to tetracyclic condensed ring groups each having carbon atoms and further having one to four heteroatoms selected from oxygen, sulfur, and nitrogen, such as indolyl group, benzofuryl group, benzothiazolyl group, benzoxazolyl group, xanthenyl group, benzimidazolyl group, quinolyl group, isoquinolyl group, phthalazinyl group, quinazolinyl group, quinoxalinyl group, indolizinyl group, quinolizinyl group, 1,8-naphthyridinyl group, dibenzofuranyl group, carbazolyl group, acridinyl group, phenanthridinyl group, perimidinyl group, phenazinyl group, chromanyl group, phenothiazinyl group, phenoxazinyl group, and 7H-pirazino[2,3-c]carbazolyl group.

In the present invention, the "optionally substituted amino group" used for, for example, $R_1$ in the Formula (I) refers to a primary amino group, a secondary amino group, or a tertiary amino group. The primary amino group refers to —$NH_2$ group. The secondary amino group is an amino group having one substituent. Examples of the secondary amino group can include, but are not limited to, alkylamino groups, arylamino groups, and alkoxycarbonylamino groups. In addition, the tertiary amino group refers to an amino group having two identical or different substituents. Examples of the tertiary amino group can include, but are not limited to, dialkylamino groups and diarylamino groups.

In the Formula (I) that represents a compound according to the present invention, $R_2$ represents an optionally substituted aryl group containing a condensed ring system with three or more rings, a substituted naphthyl group, or a group represented by the following Formula (II), (III), (IV), or (V).

In a compound according to the present invention, the naphthyl moiety, the carboxylic acid moiety, and the $R_2$ moiety are considered to be particularly involved in the inhibitory activity against the function of Pin1. The $R_2$ moiety can have any of a wide variety of chemical structures containing an aromatic or heterocyclic ring.

In the present invention, the "aryl group containing a condensed ring system with three or more rings" refers to a group derived from an aromatic compound containing a condensed ring system with three or more carbocycles.

The "aryl group containing a condensed ring system with three or more rings" is preferably a tricyclic aryl group.

Examples of the "aryl group containing a condensed ring system with three or more rings" in the present invention can include, but are not limited to, fluorenyl group, anthryl group, biphenylenyl group, indacenyl group, phenanthrenyl group, as-indacenyl group, s-indacenyl group, acenaphthylenyl group, phenalenyl group, fluoranthenyl group, pyrenyl group, naphthacenyl group, and hexacenyl group.

The chemical structure of the "optionally substituted aryl group containing a condensed ring system with three or more rings" in the present invention can be specifically illustrated by, but not limited to, those of the following groups.

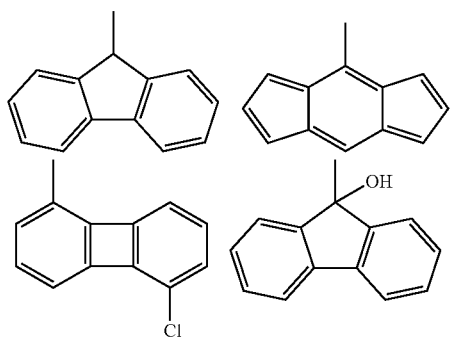

The $R_2$ in the Formula (I) can be a substituted naphthyl group, and examples of the substituted naphthyl group can include, but are not limited to, 6-methoxycarbonyl-2-naphthyl group and 5-methyl-1-naphthyl group.

The $R_2$ in the Formula (I) can be a group represented by the Formula (II), and the structure of the Formula (II) is illustrated below:

(II)

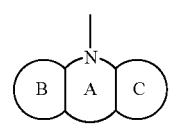

(wherein a ring A represents an optionally substituted monocyclic heterocyclic group, and rings B and C independently represent an optionally substituted monocyclic or polycyclic aryl or heterocyclic group, and the rings A, B, and C together form a condensed ring system).

In the Formula (II), each of the rings B and C preferably represents a benzene ring.

The chemical structure of the group represented by the Formula (II) can be specifically illustrated by, but not limited to, those of the following groups.

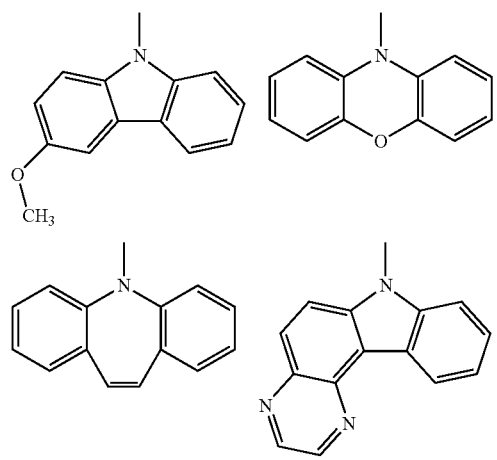

The $R_2$ in the Formula (I) can be a group represented by the Formula (III), and the structure of the Formula (III) is illustrated below:

(III)

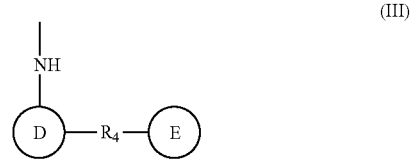

(wherein rings D and E independently represent an optionally substituted monocyclic or polycyclic aryl or heterocyclic group, and $R_4$ represents a divalent oxy or carbonyl group).

The chemical structure of the group represented by the Formula (III) can be specifically illustrated by, but not limited to, those of the following groups.

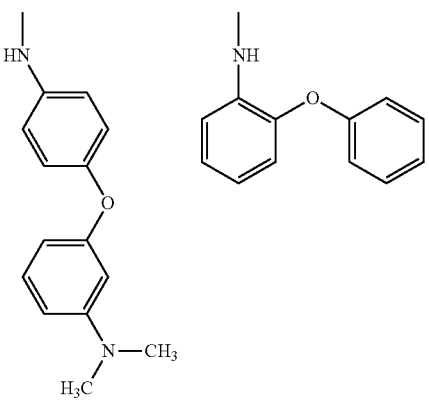

The R₂ in the Formula (I) can be a group represented by the Formula (IV), and the structure of the Formula (IV) is illustrated below:

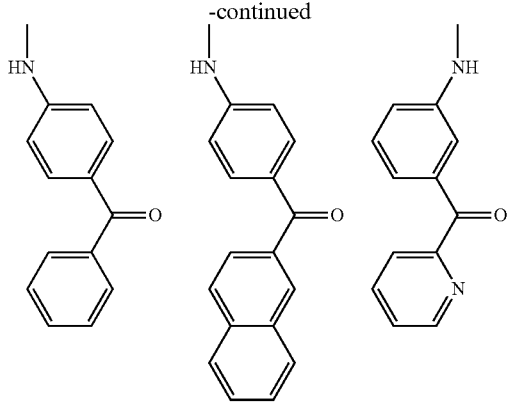

(IV)

(wherein rings D and E independently represent an optionally substituted monocyclic or polycyclic aryl or heterocyclic group).

The chemical structure of the group represented by the Formula (IV) can be specifically illustrated by, but not limited to, those of the following groups.

The R₂ in the Formula (I) can be a group represented by the Formula (V), and the structure of the Formula (V) is illustrated below:

(V)

(wherein R₄ represents 0 to 7 identical or different substituents attached to the naphthyl group, and Y represents a —NH— group or an alkylene group containing one or two carbon atoms).

The chemical structure of the group represented by the Formula (V) can be specifically illustrated by, but not limited to, those of the following groups.

The R₂ in the Formula (I) that represents a compound according to the present invention is preferably a group represented by the above Formula (II), (III), or (IV). More preferably, the R₂ is a group represented by the above Formula (II).

In the Formula (I) that represents a compound according to the present invention, R₃ represents 0 to 7 identical or different substituents attached to the naphthyl group.

R₃ may be attached to the naphthyl group at any of positions 1 through 8. However, R₃ is not allowed to be attached to the naphthyl group at the position where the chain moiety of the compound according to the present invention is attached. In addition, R₃ may also be unattached to the naphthyl group, which results in formation of an unsubstituted naphthyl group. In cases where R₃ is attached to the naphthyl group, the number of R₃ can be from 1 to 7, and the substituents represented by R₃ may be different from each other or be wholly or partly identical. R₃ is preferably a substituent containing 1 to 10 atoms.

In the Formula (I) that represents a compound according to the present invention, X represents a single bond, —CH₂— group, or —NH— group.

X preferably represents a single bond. In cases where X represents a single bond, the above Formula (I) can alternatively be illustrated by the following Formula (XVI):

(XVI)

(wherein m, n, R₁, R₂, and R₃ are the same as defined above).

The "substituent" as used in the present invention is a halogen (such as, for example, fluorine, chlorine, bromine, or iodine), an alkyl group (for example, a $C_{1-6}$ alkyl group, such as methyl group, ethyl group, propyl group, isopropyl group, butyl group, isobutyl group, sec-butyl group, tert-butyl group, pentyl group, or hexyl group), a cycloalkyl group (for example, a $C_{3-6}$ cycloalkyl group, such as cyclopropyl group, cyclobutyl group, cyclopentyl group, or cyclohexyl group), an alkynyl group (for example, a $C_{2-6}$ alkynyl group, such as ethynyl group, 1-propynyl group, or propargyl group), an alkenyl group (for example, a $C_{2-6}$ alkenyl group, such as vinyl group, allyl group, isopropenyl group, butenyl group, or isobutenyl group), an aralkyl group (for example, a $C_{7-11}$ aralkyl group, such as benzyl group, α-methylbenzyl group, or phenethyl group), an aryl group (for example, a $C_{6-10}$ aryl group, such as phenyl group or naphthyl group; preferably phenyl group), an alkoxy group (for example, a $C_{1-6}$ alkoxy group, such as methoxy group, ethoxy group, propoxy group, isopropoxy group, butoxy group, isobutoxy group, sec-butoxy group, or tert-butoxy), an aryloxy group (for example, a $C_{6-10}$ aryloxy group, such as phenoxy), an alkanoyl group (for example, a $C_{1-6}$ alkyl-carbonyl group, such as formyl group, acetyl group, propionyl group, butyryl group, or isobutyryl group), an arylcarbonyl group (for example, a $C_{6-10}$ aryl-carbonyl group, such as benzoyl group or naphthoyl group), an alkanoyloxy group (for example, a $C_{1-6}$ alkyl-carbonyloxy group, such as formyloxy group, acetyloxy group, propionyloxy group, butyryloxy group, or isobutyryloxy group), an arylcarbonyloxy group (for example, a $C_{6-10}$ aryl-carbonyloxy group, such as benzoyloxy group or naphthoyloxy group), carboxyl group, an alkoxycarbonyl group (for example, a $C_{1-6}$ alkoxycarbonyl group, such as methoxycarbonyl group, ethoxycarbonyl group, propoxycarbonyl group, isopropoxycarbonyl group, butoxycarbonyl group, isobutoxycarbonyl group, or tert-butoxycarbonyl), an aralkyloxycarbonyl group (for example, a $C_{7-11}$ aralkyloxycarbonyl group, such as benzyloxycarbonyl group), carbamoyl group, a halogenated alkyl group (for example, a mono-, di-, or tri-halogenated —$C_{1-4}$ alkyl group, such as chloromethyl group, dichloromethyl group, trifluoromethyl group, or 2,2,2-trifluoroethyl group), oxo group, amidino group, imino group, amino group, an alkylamino group (for example, a mono-$C_{1-4}$ alkylamino group, such as methylamino group, ethylamino group, propylamino group, isopropylamino group, or butylamino group), a dialkylamino group (for example, a di-$C_{1-4}$ alkylamino group, such as dimethylamino group, diethylamino group, dipropylamino group, diisopropylamino group, dibutylamino group, or methylethylamino group), an alkoxycarbonylamino group (for example, a $C_{1-6}$ alkoxycarbonylamino group, such as methoxycarbonylamino group, isoproxycarbonylamino group, or tert-butoxycarbonylamino group), a cyclic amino group (a 3- to 6-membered cyclic amino group containing carbon atoms and one nitrogen atom and further containing one to three heteroatoms selected from oxygen, sulfur, and nitrogen; such as, for example, aziridinyl group, azetidinyl group, pyrrolidinyl group, pyrrolinyl group, pyrrolyl group, imidazolyl group, pyrazolyl group, imidazolidinyl group, piperidyl group, morpholinyl group, dihydropyridyl group, pyridyl group, N-methylpiperazinyl group, or N-ethylpiperazinyl group), alkylenedioxy group (for example, a $C_{1-3}$ alkylenedioxy group, such as methylenedioxy group or ethylenedioxy group), hydroxy group, cyano group, mercapto group, sulfo group, sulfino group, phosphono group, sulfamoyl group, a monoalkylsulfamoyl group (for example, a mono-$C_{1-6}$ alkylsulfamoyl group, such as N-methylsulfamoyl, N-ethylsulfamoyl, N-propylsulfamoyl, N-isopropylsulfamoyl, or N-butylsulfamoyl), a dialkylsulfamoyl group (for example, a di-$C_{1-6}$ alkylsulfamoyl group, such as N,N-dimethylsulfamoyl group, N,N-diethylsulfamoyl group, N,N-dipropylsulfamoyl group, or N,N-dibutylsulfamoyl group), an alkylthio group (for example, a $C_{1-6}$ alkylthio group, such as methylthio group, ethylthio group, propylthio group, isopropylthio group, butylthio group, sec-butylthio group, or tert-butylthio group), an arylthio group (for example, a $C_{6-10}$ arylthio group, such as phenylthio group or naphthylthio group), an alkylsulfinyl group (for example, a $C_{1-6}$ alkylsulfinyl group, such as methylsulfinyl group, ethylsulfinyl group, propylsulfinyl group, or butylsulfinyl group), an alkylsulfonyl group (for example, a $C_{1-6}$ alkylsulfonyl group, such as methylsulfonyl group, ethylsulfonyl group, propylsulfonyl group, or butylsulfonyl group), or an arylsulfonyl group (for example, a $C_{6-10}$ arylsulfonyl group, such as phenylsulfonyl group or naphthylsulfonyl group).

In cases where the "substituent" is a substituent containing 1 to 10 atoms, the number of atoms in the substituent is from 1 to 10. Examples of a substituent that can be used in the present invention include, but are not limited to, halogens, methyl group, ethyl group, vinyl group, methoxy group, ethoxy group, acetyl group, carboxyl group, methoxycarbonyl group, chloromethyl group, primary amino group, methylamino group, dimethylamino group, hydroxy group, sulfo group, and methylthio group.

In the present invention, the phrase "optionally substituted" means that a substituent as described above is present or absent. In cases where a moiety is substituted, two or more substituents may be present within the moiety, and the substituents may be identical to or different from each other. In cases where a compound according to the present invention is "optionally substituted," the number of substituents within the compound is preferably from 0 to 3.

1-2. Salts of Compounds

A salt of a compound according to the present invention may be a salt with, for example, an inorganic or organic base, an inorganic or organic acid, or an acidic or basic amino acid. In cases where a compound represented by the Formula (I) according to the present invention has an acidic functional group, a salt of the compound can be formed with an inorganic base, an organic base, or a basic amino acid. Additionally, in cases where a compound represented by the Formula (I) according to the present invention has a basic functional group, a salt of the compound can be formed with an inorganic acid, an organic acid, or an acidic amino acid.

Examples of the salt with an inorganic base include, but are not limited to, sodium, potassium, and ammonium salts. Examples of the salt with an organic base include, but are not limited to, trimethylamine, ethanolamine, and cyclohexylamine salts. Examples of the salt with an inorganic acid include, but are not limited to, hydrochloride and phosphate salts. Examples of the salt with an organic acid include, but are not limited to, acetate, phthalate, fumarate, and oxalate salts. Examples of the salt with an acidic amino acid include, but are not limited to, salts with aspartic acid and with glutamic acid, while examples of the salt with a basic amino acid include salts with arginine and with lysine.

1-3. Methods for Compound Production

A compound according to the present invention can be synthesized by, for example, but not limited to, using an amino acid derivative containing a naphthyl group as a starting material, according to the scheme shown in the following reaction flow chart:

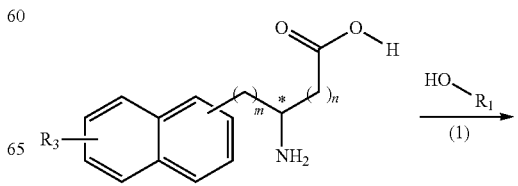

-continued

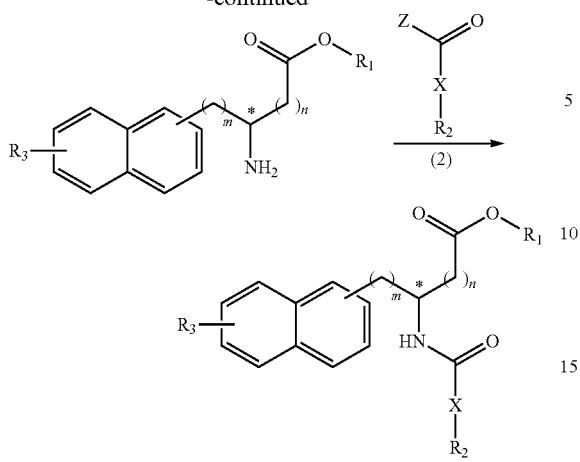

(wherein m, n, $R_1$, $R_2$, $R_3$, and X are the same as defined above, and Z represents a hydroxyl group or a chlorine atom).

In the above scheme, the reaction (1) is a reaction in which the carboxylic acid moiety of an amino acid derivative containing a naphthyl group is allowed to react with an $R_1$-containing alcohol through condensation reaction and thereby to attach $R_1$ to the amino acid derivative containing a naphthyl group via an ester bond. Moreover, the reaction (2) is a reaction in which the amino group of the compound prepared by the reaction (1) is allowed to react with a carboxylic acid or acid chloride containing $R_2$ and X through condensation reaction and thereby to attach X and $R_2$ to the above compound via an amide bond.

In cases where a compound according to the present invention in which $R_1$ is H is synthesized according to the above scheme, the compound in which $R_1$ is H can be obtained by, for example, hydrolysis of the product after the reactions (1) and (2) to remove $R_1$. Alternatively, the compound in which $R_1$ is H can also be obtained by allowing an amino acid derivative containing a naphthyl group in which $R_1$ is a hydrogen atom to react directly with a carboxylic acid containing $R_2$ and X through condensation reaction, bypassing the reaction (1).

Additionally, in cases where a compound according to the present invention is a compound with a urea bond, namely a compound in which, for example, X represents a —NH— group, the compound can also be synthesized according to the scheme shown in the following reaction flow chart:

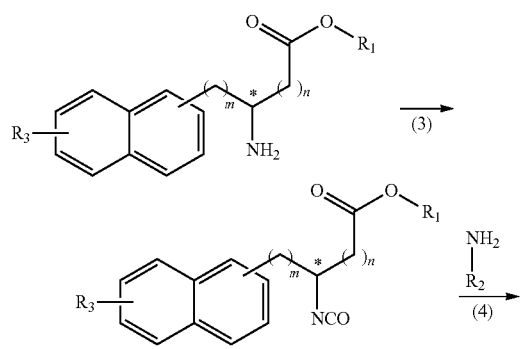

-continued

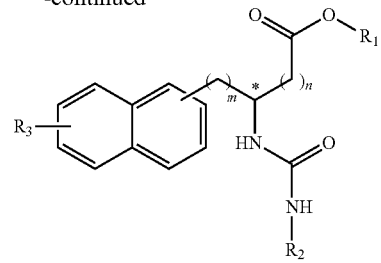

(wherein m, n, $R_1$, $R_2$, and $R_3$ are the same as defined above).

In the above scheme, the reaction (3) is a reaction in which the amino group of an amino acid derivative containing a naphthyl group is allowed to react with phosgene to produce an isocyanate group. Moreover, the reaction (4) is a reaction in which the isocyanate group of the compound prepared by the reaction (3) is allowed to react with an amino group containing $R_2$ and thereby to attach $R_2$ to the above compound via a urea bond.

Additionally, the compound with a urea bond may be synthesized by allowing an $R_2$-connected isocyanate group to react with the amino group of an amino acid derivative containing a naphthyl group, according to the scheme shown in the following reaction flow chart:

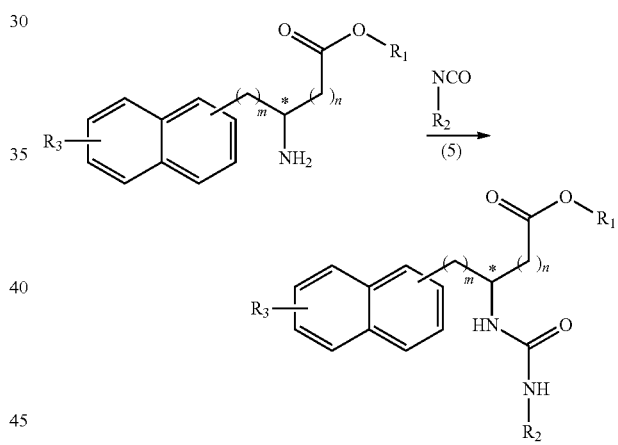

(wherein m, n, $R_1$, $R_2$, and $R_3$ are the same as defined above).

2. Pin1 Inhibitors

Pin1 refers to a kind of peptidyl-prolyl cis-trans isomerase (PPIase) that catalyzes cis/trans isomerization of proline residues in proteins, and is an enzyme that specifically acts on proline residues immediately preceded by phosphorylated serine or threonine to change the conformation of those proline residues.

A Pin1 inhibitor according to the present invention is a compound that inhibits the function of Pin1, and a compound represented by the Formula (I) described in the above section 1-1, or a salt thereof, can be used as the Pin1 inhibitor.

In the present invention, the phrase "inhibit the function of Pin1" means inhibiting the isomerase activity of Pin1 and/or the activity of Pin1 to associate or interact with another protein, such as IRS-1.

The activity of a Pin1 inhibitor according to the present invention to inhibit the function of Pin1 can be measured by, for example, but not limited to, examining AMPK (AMP-activated protein kinase) phosphorylation level as an index (see Yusuke Nakatsu et al., Journal of Biological Chemistry, 2015, Vol. 290, No. 40, pp. 24255-24266). Alternatively, the activity of a Pin1 inhibitor according to the present invention to inhibit the function of Pin1 can also be measured by detecting a change in the isomerase activity of Pin1 against a peptide substrate as a change in absorbance (see Hailong Zhao et al., Bioorganic & Medicinal Chemistry, 2016, Vol. 24, pp. 5911-5920). Alternatively, the activity of a Pin1 inhibitor according to the present invention to inhibit the function of Pin1 can also be measured by detecting the association of the inhibitor with Pin1, which competes with the association of Pin1 with a peptide substrate (see Shuo Wei et al., Nature Medicine, Vol. 21, No. 5, pp. 457-466, online methods).

3. Pharmaceutical Compositions

A pharmaceutical composition according to the present invention is a composition comprising a compound represented by the Formula (I) or a pharmaceutically acceptable salt thereof and a pharmaceutically acceptable carrier.

The structure of the compound represented by the Formula (I) is as described in the above section 1-1.

Pharmaceutical compositions according to the present invention can inhibit the function of Pin1 as a mechanism of action to treat or prevent various diseases.

In cases where the compound represented by the Formula (I) has an acidic functional group in the molecule, examples of a pharmaceutically acceptable salt of the compound can include, but are not limited to, sodium, potassium, and ammonium salts. Additionally, in cases where the compound has a basic functional group in the molecule, examples of a pharmaceutically acceptable salt of the compound can include, but are not limited to, hydrochloride, phosphate, acetate, phthalate, fumarate, and oxalate salts.

A pharmaceutical composition according to the present invention can be prepared by combining a compound represented by the Formula (I) or a pharmaceutically acceptable salt thereof and a pharmaceutically acceptable carrier, and may be made in the form of, for example, but not limited to, tablets, granules, capsules, powders, liquids, injection solutions, suppositories, patches, eye drops, and inhalants.

As a pharmaceutically acceptable carrier used in a pharmaceutical composition according to the present invention, various inorganic or organic carrier materials can be used. When the pharmaceutical composition is prepared in solid formulation, such as a tablet or a granule, an excipient, a lubricant, a binder, a disintegrator, and the like can be used. When the pharmaceutical composition is prepared in liquid formulation, such as a liquid or an injection solution, a solvent, a solubilizing agent, a suspending agent, a buffering agent, and the like can be used.

Moreover, additives such as antioxidant, antiseptic agent, and coloring agent can also be used as necessary.

Non-limiting examples of an excipient that can be used include lactose, D-mannitol, and starch; non-limiting examples of a lubricant that can be used include magnesium stearate and talc; non-limiting examples of a binder that can be used include crystalline cellulose and gelatin; non-limiting examples of a disintegrator that can be used include carboxymethyl cellulose.

Moreover, examples of a solvent that can be used include distilled water, alcohols, and propylene glycol; examples of a solubilizing agent that can be used include polyethylene glycol and ethanol; examples of a suspending agent that can be used include stearyl triethanolamine and sodium lauryl sulfate; examples of a buffering agent that can be used include phosphate and acetate salts.

4. Therapeutic or Prophylactic Agents for Inflammatory Disease with Fibrosis

Therapeutic or prophylactic agents for inflammatory diseases associated with fibrosis according to the present invention contain a compound represented by the Formula (I) or a pharmaceutically acceptable salt thereof as an active ingredient.

The structure of the compound represented by the Formula (I) is as described in the above section 1-1, while the pharmaceutically acceptable salt thereof is as described in the above section 3.

In the present invention, inflammatory diseases associated with fibrosis refer to diseases that lead to fibrosis due to chronic tissue inflammation, including non-alcoholic steatohepatitis, inflammatory bowel disease, and pulmonary fibrosis.

In the present invention, "non-alcoholic steatohepatitis," which is also called NASH (Non-Alcoholic SteatoHepatitis), refers to a severe type of non-alcoholic fatty liver disease characterized by an accumulation of fat in the liver, which is similar to that found in cases of alcoholic hepatitis and is observed even in a patient who has no history of alcohol intake sufficient to induce liver injury. Non-alcoholic steatohepatitis is known to cause liver cirrhosis, in which dead liver cells are replaced by fibrous tissue.

In the present invention, "inflammatory bowel disease" is a collective term for diseases that cause chronic inflammation and/or ulcers in the mucosa of the large and small intestinal tracts. Ulcerative colitis and Crohn's disease are included as representative examples of inflammatory bowel disease. Ulcerative colitis is a disease that causes chronic inflammation and ulcers in the large intestine, while Crohn's disease is a disease that causes inflammatory lesions, such as ulcer and swelling, in any part of the digestive tract. In cases of stenosis due to intestinal fibrosis caused by inflammatory bowel disease, surgery should be performed.

In the present invention, "pulmonary fibrosis" is a disease that causes chronic inflammation in lung tissue, which is followed by hardening of the inflamed lung tissue due to fibrosis, and eventually impairs lung expansion and contraction.

The therapeutic or prophylactic agents for inflammatory diseases associated with fibrosis according to the present invention contain a compound represented by the Formula (I) or a pharmaceutically acceptable salt thereof as an active ingredient and thereby have an alleviating effect on the conditions of inflammatory diseases associated with fibrosis, such as non-alcoholic steatohepatitis (NASH), inflammatory bowel disease, and pulmonary fibrosis, or a prophylactic effect on the development of inflammatory diseases associated with fibrosis. Such beneficial effects are considered to be based on inhibition of Pin1 function as the mechanism of action of the compound represented by the Formula (I) or the pharmaceutically acceptable salt thereof.

In the therapeutic or prophylactic agents for inflammatory diseases associated with fibrosis according to the present invention, the compound represented by the Formula (I) and contained as an active ingredient is highly variable in terms of chemical structure, due to, for example, $R_1$, $R_2$, and $R_3$. Thus, the chemical structures of the therapeutic or prophylactic agents for inflammatory diseases associated with fibrosis according to the present invention can be modified to obtain, for example, suitable absorption, distribution, degradation, and excretion features.

The therapeutic or prophylactic agents for inflammatory diseases associated with fibrosis according to the present invention can be administered as therapeutic or prophylactic agents for inflammatory diseases associated with fibrosis, such as non-alcoholic steatohepatitis, inflammatory bowel disease, and pulmonary fibrosis, not only to patients diagnosed with these diseases but also to patients suspected of having or at risk of these diseases.

The therapeutic or prophylactic agents for inflammatory diseases associated with fibrosis according to the present invention may be formulated in various dosage forms, which are combined with pharmaceutically acceptable carriers, as described in the above section 3.

When used as a therapeutic or prophylactic agent for non-alcoholic steatohepatitis, the therapeutic or prophylactic agent can be made in the form of, for example, but not limited to, tablets, granules, capsules, powders, and liquids for oral administration, and can also be administered in the form of injection solution directly to the liver by, for example, tube feeding, from the viewpoint of allowing the therapeutic or prophylactic agent to act directly on the liver and thereby to reduce side effects.

When used as a therapeutic or prophylactic agent for inflammatory bowel disease, the therapeutic or prophylactic agent is preferably made in the form of, but not limited to, tablets, granules, capsules, powders, liquids, or suppositories, from the viewpoint of allowing the therapeutic or prophylactic agent to act directly on the intestine.

When used as a therapeutic or prophylactic agent for pulmonary fibrosis, the therapeutic or prophylactic agent is preferably made in the form of, for example, but not limited to, inhalants, from the viewpoint of allowing the therapeutic or prophylactic agent to act directly on the lung.

The therapeutic or prophylactic agents for inflammatory diseases associated with fibrosis according to the present invention should preferably be administered to a patient at a daily dose of 0.01 to 100 mg, more preferably 0.1 to 10 mg, of active ingredient per kg of body weight.

The therapeutic or prophylactic agents for inflammatory diseases associated with fibrosis according to the present invention may contain a compound according to the present invention or a pharmaceutically acceptable salt thereof and further contain active ingredients in at least one or more drugs selected from the group of therapeutic or prophylactic agents for the inflammatory diseases associated with fibrosis.

Examples of the active ingredients that can be used include, but are not limited to, adrenocorticosteroid, anti-TNFα antibodies, 5-ASA (5-aminosalicylic acid; Mesalazine), and obeticholic acid (6-ethyl-chenodeoxycholic acid).

Additionally, the therapeutic or prophylactic agents for inflammatory diseases associated with fibrosis according to the present invention may be used in combination with other therapeutic or prophylactic agents for the inflammatory diseases associated with fibrosis.

5. Therapeutic or Prophylactic Agents for Cancer

Therapeutic or prophylactic agents for cancer according to the present invention contain a compound represented by the Formula (I) or a pharmaceutically acceptable salt thereof as an active ingredient.

The structure of the compound represented by the Formula (I) is as described in the above section 1-1, while the pharmaceutically acceptable salt thereof is as described in the above section 3.

The therapeutic or prophylactic agents for cancer according to the present invention have an effect to inhibit cancer growth or an effect to prevent cancer development. Such beneficial effects are considered to be based on inhibition of Pin1 function as the mechanism of action of the compound represented by the Formula (I) or the pharmaceutically acceptable salt thereof.

The therapeutic or prophylactic agents for cancer according to the present invention can be used against cancer, such as colon cancer, prostate cancer, brain tumors, larynx cancer, lung cancer, breast cancer, esophagus cancer, gastric cancer, duodenal cancer, liver cancer, gallbladder cancer, bile duct cancer, pancreatic cancer, kidney cancer, ovarian cancer, cervical cancer, bladder cancer, testicular cancer, leukemia, lymphoma, and multiple myeloma.

The therapeutic or prophylactic agents for cancer according to the present invention can be suitably used as therapeutic or prophylactic agents for colon cancer or prostate cancer.

In the therapeutic or prophylactic agents for cancer according to the present invention, the compound represented by the Formula (I) and contained as an active ingredient is highly variable in terms of chemical structure, due to, for example, $R_1$, $R_2$, and $R_3$. Thus, the chemical structures of the therapeutic or prophylactic agents for cancer according to the present invention can be modified to obtain, for example, suitable absorption, distribution, degradation, and excretion features.

The therapeutic or prophylactic agents for cancer according to the present invention can be administered as therapeutic or prophylactic agents for cancer not only to patients diagnosed with cancer but also to patients suspected of having or at risk of cancer.

Particularly, the prophylactic agents according to the present invention are effectively administered to patients at risk of colon cancer. In this respect, examples of the patients at risk of colon cancer include, but are not limited to, patients with familial polyposis coli, Lynch syndrome, MUTYH-associated polyposis coli, Peutz-Jeghers syndrome, juvenile polyposis, Cowden disease, Crohn's disease, ulcerative colitis, Cronkhite-Canada syndrome, and the like.

The therapeutic or prophylactic agents for cancer according to the present invention may be formulated in various dosage forms, which are combined with pharmaceutically acceptable carriers, as described in the above section 3.

The therapeutic or prophylactic agents for cancer according to the present invention should preferably be administered to a patient at a daily dose of 0.01 to 100 mg, more preferably 0.1 to 10 mg, of active ingredient per kg of body weight.

The therapeutic or prophylactic agents for cancer according to the present invention may contain a compound according to the present invention or a pharmaceutically acceptable salt thereof and further contain active ingredients in at least one or more drugs selected from the group of therapeutic or prophylactic agents for cancer.

Examples of the active ingredients that can be used include, but are not limited to, oxaliplatin, cisplatin, cyclophosphamide, fluorouracil, irinotecan, doxorubicin, bevacizumab, and cetuximab.

Additionally, the therapeutic or prophylactic agents for cancer according to the present invention can be used in combination with other therapeutic or prophylactic agents for cancer.

6. Therapeutic or Prophylactic Agents for Obesity

Therapeutic or prophylactic agents for obesity according to the present invention contain a compound represented by the Formula (I) or a pharmaceutically acceptable salt thereof as an active ingredient.

The structure of the compound represented by the Formula (I) is as described in the above section 1-1, while the pharmaceutically acceptable salt thereof is as described in the above section 3.

The therapeutic or prophylactic agents for obesity according to the present invention have an effect to reduce accumulation of body fat and thereby to treat or prevent obesity. Such beneficial effects are considered to be based on inhibition of Pin1 function as the mechanism of action of the compound represented by the Formula (I) or the pharmaceutically acceptable salt thereof.

In the therapeutic or prophylactic agents for obesity according to the present invention, the compound represented by the Formula (I) and contained as an active ingredient is highly variable in terms of chemical structure, due to, for example, $R_1$, $R_2$, and $R_3$. Thus, the chemical structures of the therapeutic or prophylactic agents for obesity according to the present invention can be modified to obtain, for example, suitable absorption, distribution, degradation, and excretion features.

In the present invention, "obesity" refers to a condition with excessive fat accumulation in the internal organs or under the skin, which can be diagnosed with, for example, abdominal fat area measured by abdominal CT scanning. The therapeutic or prophylactic agents for obesity according to the present invention can be administered as therapeutic or prophylactic agents for obesity not only to patient diagnosed with obesity but also to patients suspected of having or at risk of obesity.

The therapeutic or prophylactic agents for obesity according to the present invention may be formulated in various dosage forms, which are combined with pharmaceutically acceptable carriers, as described in the above section 3.

The therapeutic or prophylactic agents for obesity according to the present invention should preferably be administered to a patient at a daily dose of 0.01 to 100 mg, more preferably 0.1 to 10 mg, of active ingredient per kg of body weight.

The therapeutic or prophylactic agents for obesity according to the present invention may contain a compound according to the present invention or a pharmaceutically acceptable salt thereof and further contain active ingredients in at least one or more drugs selected from the group of therapeutic or prophylactic agents for obesity.

Examples of the active ingredients that can be used include, but are not limited to, cetilistat, orlistat, and lorcaserin.

Additionally, the therapeutic or prophylactic agents for obesity according to the present invention can be used in combination with other therapeutic or prophylactic agents for obesity.

EXAMPLES

Now, the present invention will be described in detail by reference to examples, but the present invention is not limited thereto.

Example 1

Synthesis of Compounds (Example 1-1) Synthesis of Intermediates

Intermediates (H-34, H-47, and H-48) used for the synthesis of compounds according to the present invention were produced.

Thionyl chloride (4.9 g, 3.0 mL, 41 mmol) was added to a solution of D-naphthylalanine (5.0 g, 23.2 mmol) in methanol (100 mL) at room temperature, and the resulting mixture was stirred at the same temperature for 16 hours. The mixture was concentrated under reduced pressure. Toluene was added to the residue, and thionyl chloride was removed from the residue by repeating the concentration step under reduced pressure several times to give H-34 represented by the following structural formula as a white powder (6.2 g, 23.2 mmol, 100%).

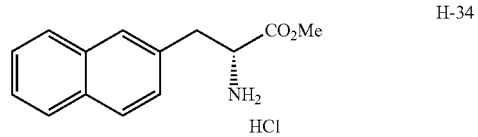 [SMILES: COC(=O)[C@H](N)Cc1ccc2ccccc2c1 ; Cl]

To a solution of H-34 hydrochloride (400 mg, 1.4 mmol) in dichloromethane (3 mL), saturated aqueous sodium bicarbonate solution (3 mL) at 0° C. and then a solution of triphosgene (178 mg, 0.6 mmol) in dichloromethane (1 mL) at the same temperature were added, and the resulting mixture was stirred at the same temperature for 15 minutes. The mixture was extracted with chloroform. The organic layer was washed with saturated brine, dried over anhydrous magnesium sulfate, and then filtered and concentrated under reduced pressure to give H-48 represented by the following structural formula. The obtained product was used without further purification at the next step.

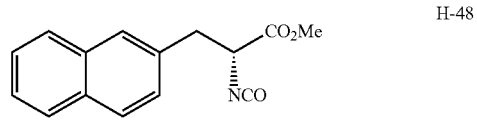

A solution of D-naphthylalanine (3.0 g, 13.9 mmol), benzyl alcohol (22.5 g, 21 mL, 209 mmol), and p-toluenesulfonic acid monohydrate (4.0 g, 20.9 mmol) in benzene (180 mL) was azeotropically dehydrated under reflux with stirring for 3 days. The mixture was cooled down to room temperature, diluted with ethyl acetate, and then washed three times with saturated sodium bicarbonate solution. The organic layer was washed with saturated brine, dried over anhydrous magnesium sulfate, and then filtered and concentrated under reduced pressure. Hydrochloric acid at a concentration of 1 M was added to the residue, and the obtained powder was suspended in ether, and then filtered under reduced pressure. The solid was washed several times with ether to give H-47 represented by the following structural formula as a white powder (4.59 g, 13.5 mmol, 97%).

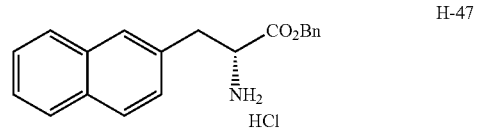 [SMILES: N[C@H](Cc1ccc2ccccc2c1)C(=O)OCc1ccccc1 ; Cl]

(Example 1-2) Synthesis of H-53

To a solution of H-47 hydrochloride (200 mg, 0.587 mmol) and 6-methoxycarbonyl-2-naphthalenecarboxylic acid (149 mg, 0.646 mmol) in DMF (2 mL), N-methylmorpholine (178 mg, 0.19 mL, 1.76 mmol) at room temperature and then 1-ethyl-3-(3-dimethylaminopropyl)carbodiimide hydrochloride (146 mg, 0.763 mmol) at the same temperature were added, and the resulting mixture was stirred at the same temperature for 2 days. Water was added to the mixture, and the resulting mixture was extracted with ethyl acetate. The organic layer was washed with saturated brine, dried over anhydrous magnesium sulfate, and then filtered and concentrated under reduced pressure. The residue was purified by silica gel column chromatography (hexane:ethyl acetate, 3:1) to give H-53 as a white powder (63 mg, 0.338 mmol, 21%).

The measured NMR spectrum and HR-ESI-MS result of H-53 are described below.

$^1$H NMR (400 MHz, CDCl$_3$) δ 3.45 (1H, dd, J=14.2, 5.5 Hz), 3.17 (1H, dd, J=14.2, 5.9 Hz), 3.99 (3H, s), 5.17 (1H, d, J=11.9 Hz), 5.24-5.31 (1H, m), 5.27 (1H, d, J=11.9 Hz), 6.77 (1H, d, J=7.8 Hz), 7.17 (1H, dd, J=8.2, 1.8 Hz), 7.28-7.39 (5H, m), 7.43-7.49 (2H, m), 7.52 (1H, bs), 7.63-7.68 (1H, m), 7.71 (1H, d, J=8.3 Hz), 7.78-7.86 (2H, m), 7.89 (1H, d, J=8.7 Hz), 7.99 (1H, d, J=8.7 Hz), 8.10 (1H, dd, J=8.7, 1.4 Hz), 8.21 (1H, s), 8.62 (1H, s); HRESIMS calcd for C$_{33}$H$_{27}$NO$_5$Na [M+Na]$^+$ 540.1787, found 540.1787.

The identified chemical structure of H-53 is indicated below.

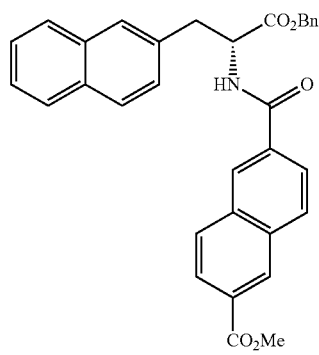

H-53

(Example 1-3) Synthesis of H-62

To a solution of H-53 (63 mg, 0.122 mmol) in THF (2 mL), 5% Pd/C (50 mg) was added, and the resulting mixture was stirred under hydrogen atmosphere at room temperature for 16 hours. The reaction mixture was filtered using celite. After the residue was washed with ethyl acetate, the resulting wash solution was concentrated under reduced pressure to give H-62 as a white powder (48 mg, 0.112 mmol, 92%).

The measured NMR spectrum and HR-ESI-MS result of H-62 are described below.

$^1$H NMR (400 MHz, CDCl$_3$) δ 3.47 (1H, dd, J=13.7, 6.0 Hz), 3.58 (1H, dd, J=13.7, 5.5 Hz), 3.98 (3H, s), 5.23 (1H, ddd, J=7.3, 6.0, 5.5 Hz), 6.86 (1H, d, J=7.3 Hz), 7.35 (1H, d, J=7.7 Hz), 7.40-7.48 (2H, m), 7.68 (1H, bs), 7.70-7.82 (5H, m), 7.88 (1H, d, J=8.7 Hz), 8.03 (1H, d, J=8.2 Hz), 8.12 (1H, bs), 8.54 (1H, bs); HRESIMS calcd for C$_{26}$H$_{21}$NO$_5$Na [M+Na]$^+$450.1317, found 450.1317.

The identified chemical structure of H-62 is indicated below.

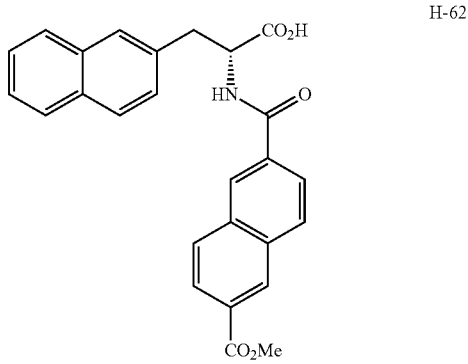 [SMILES: COC(=O)c1ccc2cc(C(=O)N[C@H](Cc3ccc4ccccc4c3)C(=O)O)ccc2c1]

H-62

(Example 1-4) Synthesis of H-85

To a solution of H-34 hydrochloride (200 mg, 0.753 mmol) and 9-fluorenecarboxylic acid (174 mg, 0.83 mmol) in DMF (2 mL), N-methylmorpholine (229 mg, 0.25 mL, 2.26 mmol) at room temperature and then 1-ethyl-3-(3-dimethylaminopropyl)carbodiimide hydrochloride (188 mg, 0.98 mmol) at the same temperature were added, and the resulting mixture was stirred at the same temperature for 2 days. Water was added to the mixture, and the resulting mixture was extracted with ethyl acetate. The organic layer was washed with saturated brine, dried over anhydrous magnesium sulfate, and then filtered and concentrated under reduced pressure. The residue was purified by silica gel column chromatography (chloroform:ethyl acetate, 20:1) to give H-85 as a pale yellow powder (137 mg, 0.325 mmol, 43%).

The measured NMR spectrum and HR-ESI-MS result of H-85 are described below.

$^1$H NMR (400 MHz, CDCl$_3$) δ 3.05 (1H, dd, J=14.1, 6.4 Hz), 3.20 (1H, dd, J=14.1, 5.5 Hz), 3.65 (3H, s), 4.75 (1H, s), 4.88 (1H, ddd, J=7.8, 6.4, 5.5 Hz), 5.70 (1H, d, J=7.8 Hz), 6.89 (1H, dd, J=8.3, 1.9 Hz), 7.13-7.26 (3H, m), 7.34-7.48 (5H, m), 7.53-7.60 (3H, m), 7.70-7.79 (3H, m); HRESIMS calcd for C$_{28}$H$_{23}$NO$_3$Na [M+Na]$^+$444.1576, found 444.1575.

The identified chemical structure of H-85 is indicated below.

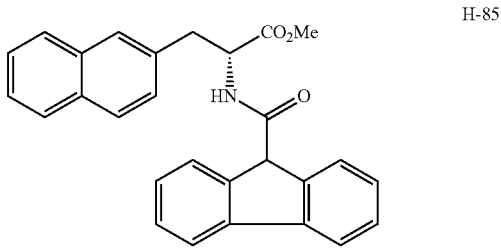 [SMILES: COC(=O)[C@@H](Cc1ccc2ccccc2c1)NC(=O)C1c2ccccc2-c2ccccc21]

H-85

(Example 1-5) Synthesis of H-101

To a solution of H-85 (130 mg, 0.31 mmol) in THF (4 mL), an aqueous lithium hydroxide solution (1 M, 1.5 mL, 1.5 mmol) was added at room temperature, and the resulting mixture was stirred at the same temperature for 4 hours. The mixture was neutralized by adding 1 M hydrochloric acid thereto, and then extracted with ethyl acetate. The organic layer was washed with saturated brine, dried over anhydrous magnesium sulfate, and then filtered and concentrated under reduced pressure to give H-101 as a pale yellow powder (110 mg, 0.26 mmol, 84%).

The measured NMR spectrum and HR-ESI-MS result of H-101 are described below.

$^1$H NMR (400 MHz, DMSOd$_6$) δ 3.23-3.37 (2H, m), 4.61 (1H, td, J=8.7, 5.0 Hz), 6.63 (1H, bs), 6.70 (1H, d, J=7.4 Hz), 6.79 (1H, t, J=7.8 Hz), 7.20-7.57 (7H, m), 7.66 (1H, d, J=7.8 Hz), 7.70 (1H, d, J=7.3 Hz), 7.76 (1H, s), 7.86 (2H, d, J=8.2 Hz), 7.92 (1H, d, J=7.7 Hz), 8.35 (1H, d, J=8.7 Hz); HRESIMS calcd for $C_{27}H_{21}NO_4Na$ [M+Na]$^+$446.1368, found 446.1365.

The identified chemical structure of H-101 is indicated below.

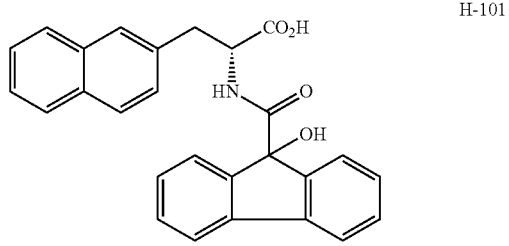 [SMILES: O=C(O)[C@@H](Cc1ccc2ccccc2c1)NC(=O)C1(O)c2ccccc2-c2ccccc21]

H-101

(Example 1-6) Synthesis of H-91

To a solution of H-34 hydrochloride (200 mg, 0.753 mmol) and 9-fluoreneacetic acid (202 mg, 0.904 mmol) in DMF (2 mL), N-methylmorpholine (229 mg, 0.25 mL, 2.26 mmol) at room temperature and then 1-ethyl-3-(3-dimethylaminopropyl)carbodiimide hydrochloride (188 mg, 0.98 mmol) at the same temperature were added, and the resulting mixture was stirred at the same temperature for 2 days. Water was added to the mixture, and the resulting mixture was extracted with ethyl acetate. The organic layer was washed with saturated brine, dried over anhydrous magnesium sulfate, and then filtered and concentrated under reduced pressure. The residue was purified by silica gel column chromatography (hexane:ethyl acetate, 2:1) to give H-91 as a white powder (182 mg, 0.418 mmol, 56%).

The measured NMR spectrum and HR-ESI-MS result of H-91 are described below.

$^1$H NMR (400 MHz, CDCl$_3$) δ 2.54 (1H, dd, J=15.1, 7.3 Hz), 2.69 (1H, dd, J=15.1, 7.3 Hz), 3.23 (1H, dd, J=13.7, 6.4 Hz), 3.33 (1H, dd, J=13.7, 6.0 Hz), 3.73 (3H, s), 4.49 (1H, t, J=7.3 Hz), 5.11 (1H, ddd, J=7.7, 6.4, 6.0 Hz), 5.84 (1H, d, J=7.7 Hz), 7.09 (1H, td, J=7.4, 1.0 Hz), 7.21 (1H, dd, J=8.3, 1.8 Hz), 7.24-7.39 (4H, m), 7.43-7.49 (3H, m), 7.53 (1H, s), 7.67-7.84 (5H, m); HRESIMS calcd for $C_{29}H_{25}NO_3Na$ [M+Na]$^+$458.1732, found 458.1732.

The identified chemical structure of H-91 is indicated below.

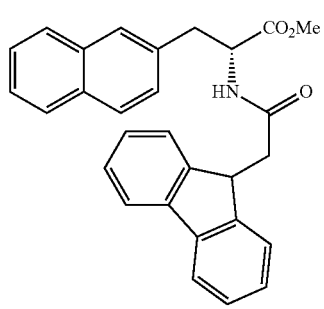

H-91

(Example 1-7) Synthesis of H-103

To a solution of H-91 (174 mg, 0.40 mmol) in THF (4 mL), an aqueous lithium hydroxide solution (1 M, 1.2 mL, 1.2 mmol) was added at room temperature, and the resulting mixture was stirred at the same temperature for 3 hours. The mixture was neutralized by adding 1 M hydrochloric acid thereto, and then extracted with ethyl acetate. The organic layer was washed with saturated brine, dried over anhydrous magnesium sulfate, and then filtered and concentrated under reduced pressure to give H-103 as a pale yellow crystal (160 mg, 0.38 mmol, 95%).

The measured NMR spectrum and HR-ESI-MS result of H-103 are described below.

$^1$H NMR (400 MHz, DMSOd$_6$) δ 2.49-2.57 (2H, m), 3.04 (1H, dd, J=13.7, 10.0 Hz), 3.28-3.33 (1H, m), 4.25 (1H, t, J=7.3 Hz), 4.76-4.83 (1H, m), 6.80 (1H, t, J=7.3 Hz), 7.14 (1H, d, J=7.4 Hz), 7.18 (1H, t, J=7.3 Hz), 7.23 (1H, t, J=7.3 Hz), 7.32 (1H, t, J=7.3 Hz), 7.43-7.51 (4H, m), 7.75-7.92 (6H, m), 8.46 (1H, d, J=8.3 Hz); HRESIMS calcd for $C_{28}H_{23}NO_3Na$ [M+Na]$^+$444.1576, found 444.1572.

The identified chemical structure of H-103 is indicated below.

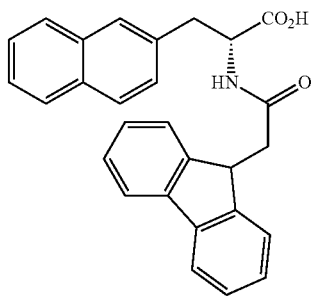

H-103

(Example 1-8) Synthesis of H-105

To a solution of H-47 hydrochloride (280 mg, 0.82 mmol) and 9-fluorenecarboxylic acid (190 mg, 0.90 mmol) in DMF (2 mL), N-methylmorpholine (332 mg, 0.36 mL, 3.28 mmol) at room temperature and then 1-ethyl-3-(3-dimethylaminopropyl)carbodiimide hydrochloride (204 mg, 1.07 mmol) at the same temperature were added, and the resulting mixture was stirred at the same temperature for 2 days. Water was added to the mixture, and the resulting mixture was extracted with chloroform. The organic layer was washed with saturated brine, dried over anhydrous magnesium sulfate, and then filtered and concentrated under reduced pressure. The residue was purified by silica gel column chromatography (chloroform:ethyl acetate, 10:1) to give H-105 as a white crystal (213 mg, 0.429 mmol, 52%).

The measured NMR spectrum and HR-ESI-MS result of H-105 are described below.

$^1$H NMR (400 MHz, CDCl$_3$) δ 3.07 (1H, dd, J=13.7, 6.4 Hz), 3.17 (1H, dd, J=13.7, 5.4 Hz), 4.74 (1H, s), 4.93 (1H, ddd, J=7.8, 6.4, 5.4 Hz), 5.00 (1H, d, J=12.3 Hz), 5.08 (1H, d, J=12.3 Hz), 5.71 (1H, d, J=7.8 Hz), 6.80 (1H, dd, J=8.7, 1.9 Hz), 7.09-7.18 (5H, m), 7.26-7.52 (10H, m), 7.68-7.76 (3H, m), 7.80-7.85 (1H, m); HRESIMS calcd for C$_{34}$H$_{27}$NO$_3$Na [M+Na]$^+$ 520.1889, found 520.1887.

The identified chemical structure of H-105 is indicated below.

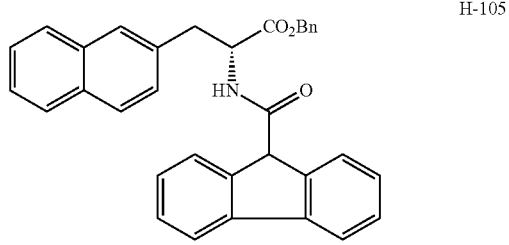 [SMILES: O=C(N[C@H](Cc1ccc2ccccc2c1)C(=O)OCc1ccccc1)C1c2ccccc2-c2ccccc21]

H-105

(Example 1-9) Synthesis of H-109

To a solution of H-105 (177 mg, 0.356 mmol) in THF (5 mL), 5% Pd/C (100 mg) was added, and the resulting mixture was stirred under hydrogen atmosphere at room temperature for 16 hours. The reaction mixture was filtered using celite. After the residue was washed with ethyl acetate, the resulting wash solution was concentrated under reduced pressure to give H-109 as a white crystal (142 mg, 0.346 mmol, 98%).

The measured NMR spectrum and HR-ESI-MS result of H-109 are described below.

$^1$H NMR (400 MHz, DMSOd$_6$) δ 3.13 (1H, dd, J=13.7, 10.1 Hz), 3.37 (1H, dd, J=13.7, 4.6 Hz), 4.59-4.67 (1H, m), 4.78 (1H, s), 6.70-6.77 (2H, m), 7.20-7.29 (2H, m), 7.34-7.40 (2H, m), 7.45 (1H, dd, J=8.7, 1.9 Hz), 7.49-7.57 (2H, m), 7.75 (1H, d, J=7.3 Hz), 7.78-7.95 (5H, m), 8.81 (1H, d, J=8.2 Hz); HRESIMS calcd for C$_{27}$H$_{21}$NO$_3$Na [M+Na]$^+$ 430.1419, found 430.1422.

The identified chemical structure of H-109 is indicated below.

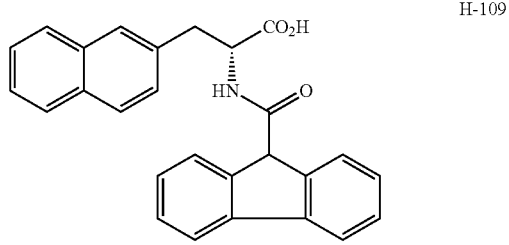 [SMILES: O=C(N[C@H](Cc1ccc2ccccc2c1)C(=O)O)C1c2ccccc2-c2ccccc21]

H-109

(Example 1-10) Synthesis of H-129

To a solution of H-34 hydrochloride (200 mg, 0.753 mmol) in dichloromethane (4 mL), triethylamine (183 mg, 0.25 mL, 1.81 mmol) at room temperature and then a solution of diphenylcarbamoyl chloride (209 mg, 0.904 mmol) in dichloromethane (1 mL) at the same temperature were added, and the resulting mixture was stirred at the same temperature for 2 days. Water was added to the mixture, and the resulting mixture was extracted with chloroform. The organic layer was washed with saturated brine, dried over anhydrous magnesium sulfate, and then filtered and concentrated under reduced pressure. The residue was purified by silica gel column chromatography (chloroform:ethyl acetate, 10:1) to give H-129 as a colorless oily substance (184 mg, 0.434 mmol, 58%).

The measured NMR spectrum and HR-ESI-MS result of H-129 are described below.

$^1$H NMR (400 MHz, CDCl$_3$) δ 3.14 (1H, dd, J=13.8, 6.4 Hz), 3.31 (1H, dd, J=13.8, 5.5 Hz), 3.74 (3H, s), 4.84-4.94 (2H, m), 7.08-7.22 (11H, m), 7.41 (1H, s), 7.45-7.52 (2H, m), 7.68-7.72 (1H, m), 7.74 (1H, d, J=8.7 Hz), 7.80-7.85 (1H, m); HRESIMS calcd for C$_{27}$H$_{24}$N$_2$O$_3$Na [M+Na]$^+$ 447.1685, found 447.1687.

The identified chemical structure of H-129 is indicated below.

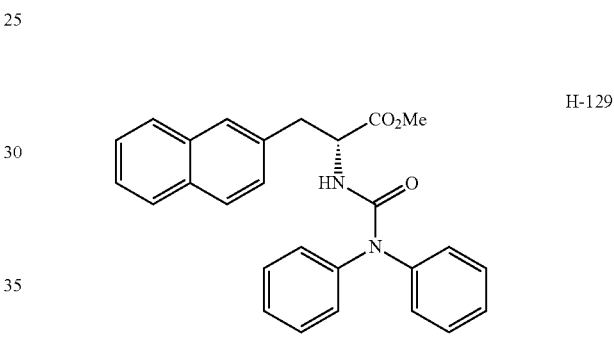

H-129

(Example 1-11) Synthesis of H-161

To a solution of H-129 (154 mg, 0.363 mmol) in THF (4 mL), an aqueous lithium hydroxide solution (1 M, 1.6 mL, 1.57 mmol) was added at room temperature, and the resulting mixture was stirred at the same temperature for 2 hours. The mixture was neutralized by adding 1 M hydrochloric acid thereto, and then extracted with ethyl acetate. The organic layer was washed with saturated brine, dried over anhydrous magnesium sulfate, and then filtered and concentrated under reduced pressure to give H-161 as an amorphous solid (145 mg, 0.354 mmol, 97%).

The measured NMR spectrum and HR-ESI-MS result of H-161 are described below.

$^1$H NMR (400 MHz, CDCl$_3$) δ 3.14 (1H, dd, J=14.2, 8.7 Hz), 3.39 (1H, dd, J=14.2, 5.1 Hz), 4.78 (1H, ddd, J=8.7, 6.8, 5.1 Hz), 4.89 (1H, d, J=6.8 Hz), 7.00-7.06 (4H, m), 7.09-7.16 (6H, m), 7.23 (1H, dd, J=8.2, 1.4 Hz), 7.41 (1H, s), 7.48-7.54 (2H, m), 7.67-7.73 (1H, m), 7.76 (1H, d, J=8.7 Hz), 7.82-7.87 (1H, m); HRESIMS calcd for C$_{26}$H$_{22}$N$_2$O$_3$Na [M+Na]$^+$ 433.1528, found 433.1525.

The identified chemical structure of H-161 is indicated below.

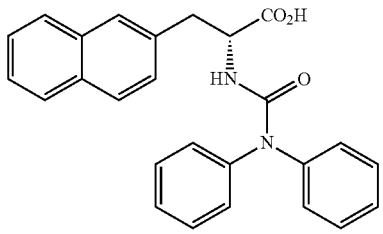 [SMILES: O=C(O)[C@@H](Cc1ccc2ccccc2c1)NC(=O)N(c1ccccc1)c1ccccc1]

H-161

(Example 1-12) Synthesis of H-138

To a solution of H-34 hydrochloride (200 mg, 0.753 mmol) and 2-naphthaleneacetic acid (168 mg, 0.904 mmol) in DMF (2 mL), N-methylmorpholine (305 mg, 0.33 mL, 3.0 mmol) at room temperature and then 1-ethyl-3-(3-dimethylaminopropyl)carbodiimide hydrochloride (188 mg, 0.98 mmol) at the same temperature were added, and the resulting mixture was stirred at the same temperature for 2 days. Water was added to the mixture, and the resulting mixture was extracted with ethyl acetate. The organic layer was washed with saturated brine, dried over anhydrous magnesium sulfate, and then filtered and concentrated under reduced pressure. The residue was purified by silica gel column chromatography (chloroform:ethyl acetate, 10:1) to give H-138 as a white crystal (174 mg, 0.438 mmol, 58%).

The measured NMR spectrum and HR-ESI-MS result of H-138 are described below.

$^1$H NMR (400 MHz, CDCl$_3$) δ 3.13 (1H, dd, J=13.7, 6.4 Hz), 3.22 (1H, dd, J=13.7, 5.5 Hz), 3.67 (1H, d, J=15.6 Hz), 3.71 (3H, s), 3.72 (1H, d, J=15.6 Hz), 4.96 (1H, ddd, J=7.8, 6.4, 5.5 Hz), 5.89 (1H, d, J=7.8 Hz), 6.95 (1H, dd, J=8.7, 1.9 Hz), 7.23 (1H, dd, J=8.2, 1.9 Hz), 7.26 (1H, s), 7.36-7.53 (6H, m), 7.61 (1H, s), 7.65-7.74 (3H, m), 7.78-7.84 (1H, m); HRESIMS calcd for C$_{26}$H$_{23}$NO$_2$Na [M+Na]$^+$420.1576, found 420.1577.

The identified chemical structure of H-138 is indicated below.

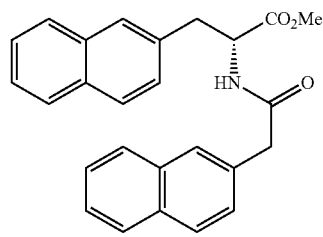 [SMILES: COC(=O)[C@@H](Cc1ccc2ccccc2c1)NC(=O)Cc1ccc2ccccc2c1]

H-138

(Example 1-13) Synthesis of H-158

To a solution of H-138 (152 mg, 0.383 mmol) in THF (4 mL), an aqueous lithium hydroxide solution (1 M, 1.5 mL, 1.53 mmol) was added at room temperature, and the resulting mixture was stirred at the same temperature for 2 hours. The mixture was neutralized by adding 1 M hydrochloric acid thereto, and then extracted with ethyl acetate. The organic layer was washed with saturated brine, dried over anhydrous magnesium sulfate, and then filtered and concentrated under reduced pressure to give H-158 as a white amorphous solid (139 mg, 0.363 mmol, 95%).

The measured NMR spectrum and HR-ESI-MS result of H-158 are described below.

$^1$H NMR (400 MHz, DMSOd$_6$) δ 3.05 (1H, dd, J=13.7, 10.0 Hz), 3.25 (1H, dd, J=13.7, 4.6 Hz), 3.53 (1H, d, J=14.2 Hz), 3.60 (1H, d, J=14.2 Hz), 4.56 (1H, ddd, J=10.0, 8.2, 4.6 Hz), 7.19 (1H, d, J=8.3 Hz), 7.36 (1H, d, J=8.2 Hz), 7.39-7.49 (4H, m), 7.56 (1H, s), 7.58-7.65 (2H, m), 7.68 (1H, s), 7.70-7.86 (4H, m), 8.51 (1H, d, J=8.2 Hz); HRESIMS calcd for C$_{25}$H$_{21}$NO$_3$Na [M+Na]$^+$406.1419, found 406.1422.

The identified chemical structure of H-158 is indicated below.

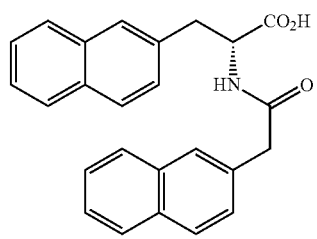 [SMILES: O=C(Cc1ccc2ccccc2c1)N[C@H](Cc1ccc2ccccc2c1)C(=O)O]

H-158

(Example 1-14) Synthesis of H-143

To a solution of H-34 hydrochloride (200 mg, 0.753 mmol) in dichloromethane (4 mL), triethylamine (183 mg, 0.25 mL, 1.81 mmol) at room temperature and then 10H-phenoxazine-10-carbonyl chloride (221 mg, 0.904 mmol) at the same temperature were added, and the resulting mixture was stirred at the same temperature for 2 days. Water was added to the mixture, and the resulting mixture was extracted with ethyl acetate. The organic layer was washed with saturated brine, dried over anhydrous magnesium sulfate, and then filtered and concentrated under reduced pressure. The residue was purified by silica gel column chromatography (hexane:ethyl acetate, 4:1) to give H-143 as a yellow oily substance (167 mg, 0.381 mmol, 51%).

The measured NMR spectrum and HR-ESI-MS result of H-143 are described below.

$^1$H NMR (400 MHz, CDCl$_3$) δ 3.23 (1H, dd, J=13.7, 6.4 Hz), 3.34 (1H, dd, J=13.7, 5.9 Hz), 3.75 (3H, s), 4.88 (1H, ddd, J=7.3, 6.4, 5.9 Hz), 5.79 (1H, d, J=7.3 Hz), 6.84 (2H, td, J=6.9, 2.3 Hz), 7.01-7.10 (4H, m), 7.21 (1H, dd, J=8.3, 1.8 Hz), 7.28 (2H, dd, J=8.2, 1.3 Hz), 7.45-7.53 (3H, m), 7.70-7.86 (3H, m); HRESIMS calcd for C$_{27}$H$_{22}$N$_2$O$_4$Na [M+Na]$^+$461.1477, found 461.1473.

The identified chemical structure of H-143 is indicated below.

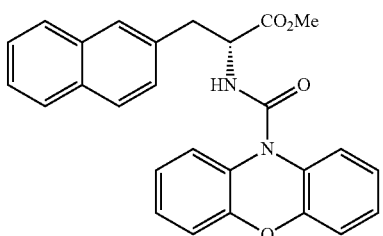

H-143

(Example 1-15) Synthesis of H-162

To a solution of H-143 (141 mg, 0.322 mmol) in THF (4 mL), an aqueous lithium hydroxide solution (1 M, 1.3 mL, 1.3 mmol) was added at room temperature, and the resulting mixture was stirred at the same temperature for 2 hours. The mixture was neutralized by adding 1 M hydrochloric acid thereto, and then extracted with ethyl acetate. The organic layer was washed with saturated brine, dried over anhydrous magnesium sulfate, and then filtered and concentrated under reduced pressure to give H-162 as an amorphous solid (133 mg, 0.314 mmol, 97%).

The measured NMR spectrum and HR-ESI-MS result of H-162 are described below.

$^1$H NMR (400 MHz, CDCl$_3$) δ 3.24 (1H, dd, J=14.2, 7.3 Hz), 3.40 (1H, dd, J=14.2, 5.5 Hz), 4.87 (1H, ddd, J=6.8, 7.3, 5.5 Hz), 5.72 (1H, d, J=6.8 Hz), 6.84 (2H, td, J=6.8, 2.3 Hz), 7.01-7.08 (4H, m), 7.19 (1H, dd, J=7.3, 1.2 Hz), 7.28 (2H, dd, J=8.4, 1.6 Hz), 7.46-7.54 (3H, m), 7.70-7.85 (3H, m); HRESIMS calcd for C$_{26}$H$_{20}$N$_2$O$_4$Na [M+Na]$^+$447.1321, found 447.1320.

The identified chemical structure of H-162 is indicated below.

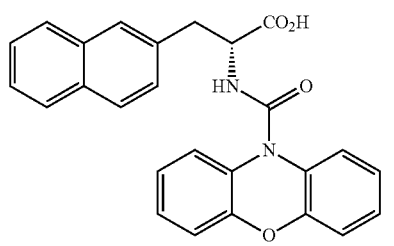 [SMILES: O=C(O)[C@@H](Cc1ccc2ccccc2c1)NC(=O)N1c2ccccc2Oc2ccccc21]

H-162

(Example 1-16) Synthesis of H-144

To a solution of H-34 hydrochloride (200 mg, 0.753 mmol) in dichloromethane (4 mL), triethylamine (183 mg, 0.25 mL, 1.81 mmol) at room temperature and then 9H-carbazole-9-carbonyl chloride (207 mg, 0.904 mmol) at the same temperature were added, and the resulting mixture was stirred at the same temperature for 2 days. Water was added to the mixture, and the resulting mixture was extracted with ethyl acetate. The organic layer was washed with saturated brine, dried over anhydrous magnesium sulfate, and then filtered and concentrated under reduced pressure. The residue was purified by silica gel column chromatography (hexane:ethyl acetate, 4:1) to give H-144 as a white crystal (210 mg, 0.381 mmol, 66%).

The measured NMR spectrum and HR-ESI-MS result of H-144 are described below.

$^1$H NMR (400 MHz, CDCl$_3$) δ 3.45 (1H, dd, J=14.2, 6.5 Hz), 3.61 (1H, dd, J=14.2, 5.4 Hz), 3.86 (3H, s), 5.19 (1H, ddd, J=7.4, 6.5, 5.4 Hz), 6.24 (1H, d, J=7.4 Hz), 7.20-7.31 (4H, m), 7.34 (1H, dd, J=8.7, 1.8 Hz), 7.45-7.51 (2H, m), 7.69 (1H, s), 7.71-7.79 (3H, m), 7.80-7.86 (2H, m), 7.95-7.99 (2H, m); HRESIMS calcd for C$_{27}$H$_{22}$N$_2$O$_3$Na [M+Na]$^+$ 445.1528, found 445.1530.

The identified chemical structure of H-144 is indicated below.

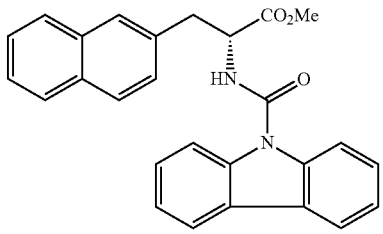

H-144

(Example 1-17) Synthesis of H-163

To a solution of H-144 (177 mg, 0.42 mmol) in THF (5 mL), an aqueous lithium hydroxide solution (1 M, 1.7 mL, 1.7 mmol) was added at room temperature, and the resulting mixture was stirred at the same temperature for 2 hours. The mixture was neutralized by adding 1 M hydrochloric acid thereto, and then extracted with ethyl acetate. The organic layer was washed with saturated brine, dried over anhydrous magnesium sulfate, and then filtered and concentrated under reduced pressure to give H-163 as a yellow crystal (158 mg, 0.386 mmol, 92%).

The measured NMR spectrum and HR-ESI-MS result of H-163 are described below.

$^1$H NMR (400 MHz, DMSOd$_6$) δ 3.28 (1H, dd, J=13.7, 11.4 Hz), 3.51 (1H, dd, J=13.7, 4.5 Hz), 4.80 (1H, ddd, J=11.4, 8.2, 4.5 Hz), 7.17 (2H, t, J=7.4 Hz), 7.24 (2H, t, J=7.4 Hz), 7.46-7.55 (4H, m), 7.61 (1H, d, J=8.7 Hz), 7.86-7.96 (4H, m), 8.09 (2H, d, J=7.7 Hz), 8.72 (1H, d, J=8.2 Hz); HRESIMS calcd for C$_{26}$H$_{20}$N$_2$O$_3$Na [M+Na]$^+$ 431.1372, found 431.1369.

The identified chemical structure of H-163 is indicated below.

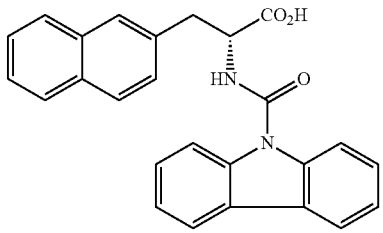

H-163

(Example 1-18) Synthesis of H-156

To a solution of H-34 hydrochloride (300 mg, 1.13 mmol) and 5H-dibenzo[b,f]azepine-5-carbonyl chloride (346 mg, 1.36 mmol) in dichloromethane (6 mL), triethylamine (366 mg, 0.50 mL, 3.62 mmol) was added at room temperature, and the resulting mixture was stirred at the same temperature for 2 days. Water was added to the mixture, and the resulting mixture was extracted with ethyl acetate. The organic layer was sequentially washed with saturated aqueous sodium bicarbonate solution and saturated brine, dried over anhydrous magnesium sulfate, and then filtered and concentrated under reduced pressure. The residue was purified by silica gel column chromatography (hexane:ethyl acetate, 6:1 to 1:1) to give H-156 as an amorphous solid (310 mg, 0.692 mmol, 61%).

The measured NMR spectrum and HR-ESI-MS result of H-156 are described below.

$^1$H NMR (400 MHz, CDCl$_3$) δ 3.10 (1H, dd, J=14.2, 6.4 Hz), 3.23 (1H, dd, J=14.2, 5.4 Hz), 3.69 (3H, s), 4.72 (1H, d, J=7.3 Hz), 4.78 (1H, ddd, J=7.3, 6.4, 5.4 Hz), 6.75 (1H, d, J=11.9 Hz), 6.86 (1H, d, J=11.9 Hz), 7.09 (1H, d, J=8.7 Hz), 7.19-7.39 (9H, m), 7.45-7.54 (2H, m), 7.68-7.74 (2H, m), 7.80-7.85 (1H, m); HRESIMS calcd for C$_{29}$H$_{24}$N$_2$O$_3$Na [M+Na]$^+$471.1685, found 471.1685.

The identified chemical structure of H-156 is indicated below.

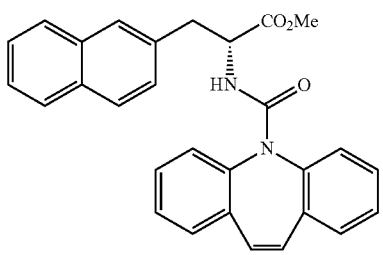 [SMILES: COC(=O)[C@@H](Cc1ccc2ccccc2c1)NC(=O)N1c2ccccc2C=Cc2ccccc21]

H-156

(Example 1-19) Synthesis of H-164

To a solution of H-156 (295 mg, 0.659 mmol) in THF (6 mL), an aqueous lithium hydroxide solution (1 M, 2.6 mL, 2.6 mmol) was added at room temperature, and the resulting mixture was stirred at the same temperature for 2 hours. The mixture was neutralized by adding 1 M hydrochloric acid thereto, and then extracted with ethyl acetate. The organic layer was washed with saturated brine, dried over anhydrous magnesium sulfate, and then filtered and concentrated under reduced pressure to give H-164 as a white crystal (242 mg, 0.558 mmol, 85%).

The measured NMR spectrum and HR-ESI-MS result of H-164 are described below.

$^1$H NMR (400 MHz, CDCl$_3$) δ 3.06 (1H, dd, J=14.2, 9.2 Hz), 3.34 (1H, bd, J=14.2 Hz), 4.51-4.60 (2H, m), 6.57 (1H, bs), 6.78 (1H, d, J=11.5 Hz), 6.97-7.37 (10H, m), 7.50-7.59 (2H, m), 7.68-7.79 (2H, m), 7.84-7.91 (1H, m); HRESIMS calcd for C$_{28}$H$_{22}$N$_2$O$_3$Na [M+Na]$^+$457.1528, found 457.1528.

The identified chemical structure of H-164 is indicated below.

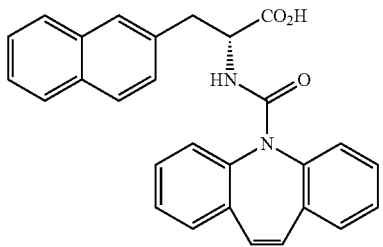 [SMILES: O=C(O)[C@@H](Cc1ccc2ccccc2c1)NC(=O)N1c2ccccc2C=Cc2ccccc21]

H-164

(Example 1-20) Synthesis of H-178

To a solution of H-164 (146 mg, 0.336 mmol) in THF (6 mL), 5% Pd/C (100 mg) was added, and the resulting mixture was stirred under hydrogen atmosphere at room temperature for 2 days. The reaction mixture was filtered using celite. After the residue was washed with ethyl acetate, the resulting wash solution was concentrated under reduced pressure to give H-178 as an amorphous solid (138 mg, 0.316 mmol, 94%).

The measured NMR spectrum and HR-ESI-MS result of H-178 are described below.

$^1$H NMR (400 MHz, CDCl$_3$) δ 2.40-3.30 (4H, m), 3.07 (1H, dd, J=14.2, 9.2 Hz), 3.39 (1H, dd, J=14.2, 5.0 Hz), 4.69 (1H, ddd, J=9.2, 6.4, 5.0 Hz), 4.82 (1H, d, J=6.4 Hz), 6.86-7.25 (9H, m), 7.35 (1H, s), 7.47-7.75 (2H, m), 7.65-7.72 (1H, m), 7.75 (1H, d, J=8.2 Hz), 7.81-7.86 (1H, m); HRESIMS calcd for C$_{28}$H$_{24}$N$_2$O$_3$Na [M+Na]$^+$459.1685, found 459.1684.

The identified chemical structure of H-178 is indicated below.

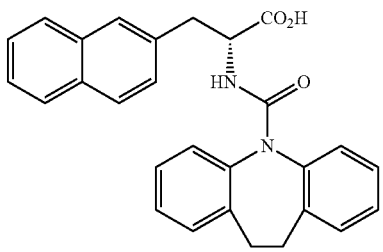 [SMILES: O=C(O)[C@@H](Cc1ccc2ccccc2c1)NC(=O)N1c2ccccc2CCc2ccccc21]

H-178

(Example 1-21) Synthesis of H-287

A solution of H-48 (200 mg, 0.784 mmol) and o-phenoxyaniline (160 mg, 0.863 mmol) in dichloromethane (2 mL) was stirred at room temperature for 8 hours. The mixture was diluted with ethyl acetate, and 1 M hydrochloric acid was added to the diluted mixture, and the resulting mixture was then extracted with ethyl acetate. The organic layer was washed with saturated brine, dried over anhydrous magnesium sulfate, and then filtered and concentrated under reduced pressure. The residue was purified by silica gel column chromatography (hexane:ethyl acetate, 3:1) to give H-287 as an amorphous solid (228 mg, 0.518 mmol, 66%).

The measured NMR spectrum and HR-ESI-MS result of H-287 are described below.

$^1$H NMR (400 MHz, CDCl$_3$) δ 3.12 (1H, dd, J=14.2, 6.4 Hz), 3.21 (1H, dd, J=14.2, 5.9 Hz), 3.65 (3H, s), 4.89 (1H, ddd, J=7.8, 6.4, 5.9 Hz), 5.45 (1H, d, J=7.8 Hz), 6.78 (1H, dd, J=7.8, 1.4 Hz), 6.90 (1H, td, J=8.2, 1.8 Hz), 6.93-7.04 (4H, m), 7.10 (1H, t, J=7.6 Hz), 7.19 (1H, dd, J=8.2, 1.8 Hz), 7.28-7.34 (2H, m), 7.40-7.46 (2H, m), 7.52 (1H, bs), 7.68-7.73 (2H, m), 7.74-7.80 (1H, m), 8.04 (1H, dd, J=8.3, 1.4 Hz); HRESIMS calcd for C$_{27}$H$_{24}$N$_2$O$_4$Na [M+Na]$^+$ 463.1634, found 463.1631.

The identified chemical structure of H-287 is indicated below.

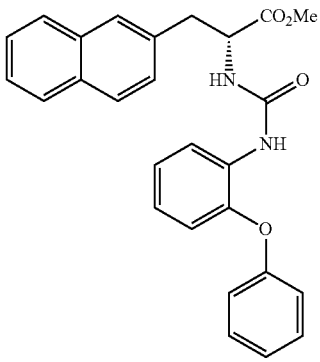 [SMILES: COC(=O)[C@@H](Cc1ccc2ccccc2c1)NC(=O)Nc1ccccc1Oc1ccccc1]

H-287

(Example 1-22) Synthesis of H-334

To a solution of H-287 (187 mg, 0.43 mmol) in THF (5 mL), an aqueous lithium hydroxide solution (1 M, 1.7 mL, 1.7 mmol) was added at room temperature, and the resulting mixture was stirred at the same temperature for 2 hours. The mixture was neutralized by adding 1 M hydrochloric acid thereto, and then extracted with ethyl acetate. The organic layer was washed with saturated brine, dried over anhydrous magnesium sulfate, and then filtered and concentrated under reduced pressure to give H-334 as a white crystal (150 mg, 0.35 mmol, 82%).

The measured NMR spectrum and HR-ESI-MS result of H-334 are described below.

$^1$H NMR (400 MHz, DMSOd$_6$) δ 3.06 (1H, dd, J=14.2, 7.3 Hz), 3.21 (1H, dd, J=14.2, 5.1 Hz), 4.55 (1H, ddd, J=7.7, 7.3, 5.1 Hz), 6.77 (1H, dd, J=8.2, 1.4 Hz), 6.86 (1H, td, J=7.7, 1.8 Hz), 6.94-6.99 (2H, m), 7.02 (1H, td, J=8.1, 1.4 Hz), 7.12 (1H, t, J=7.3 Hz), 7.23 (1H, d, J=7.7 Hz), 7.31-7.41 (3H, m), 7.41-7.49 (2H, m), 7.67 (1H, bs), 7.75-7.88 (3H, m), 8.18 (1H, dd, J=8.2, 1.4 Hz), 8.41 (1H, bs); HRESIMS calcd for C$_{26}$H$_{22}$N$_2$O$_4$Na [M+Na]$^+$449.1477, found 449.1475.

The identified chemical structure of H-334 is indicated below.

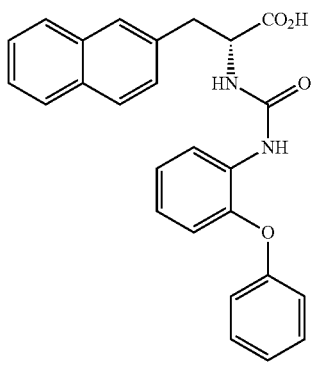 [SMILES: O=C(Nc1ccccc1Oc1ccccc1)N[C@H](Cc1ccc2ccccc2c1)C(=O)O]

H-334

(Example 1-23) Synthesis of H-291

A solution of H-48 (200 mg, 0.784 mmol) and 4-aminobenzophenone (170 mg, 0.863 mmol) in dichloromethane (2 mL) was stirred at room temperature for 18 hours. After 1 M hydrochloric acid was added to the mixture, the resulting mixture was extracted with ethyl acetate. The organic layer was washed with saturated brine, dried over anhydrous magnesium sulfate, and then filtered and concentrated under reduced pressure. The residue was purified by silica gel column chromatography (hexane:ethyl acetate, 2:1) to give H-291 as a yellow oily substance (300 mg, 0.664 mmol, 85%).

The measured NMR spectrum and HR-ESI-MS result of H-291 are described below.

$^1$H NMR (400 MHz, CDCl$_3$) δ 3.08 (1H, dd, J=14.2, 6.8 Hz), 3.22 (1H, dd, J=14.2, 5.5 Hz), 3.65 (3H, s), 4.92 (1H, ddd, J=7.8, 6.8, 5.5 Hz), 6.40 (1H, d, J=7.8 Hz), 6.59 (2H, d, J=8.7 Hz), 7.20-7.74 (14H, m), 8.32 (1H, bs); HRESIMS calcd for C$_{28}$H$_{24}$N$_2$O$_4$Na [M+Na]$^+$475.1634, found 475.1631.

The identified chemical structure of H-291 is indicated below.

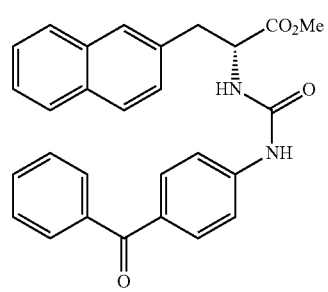 [SMILES: COC(=O)[C@@H](Cc1ccc2ccccc2c1)NC(=O)Nc1ccc(C(=O)c2ccccc2)cc1]

H-291

(Example 1-24) Synthesis of H-341

To a solution of H-291 (263 mg, 0.58 mmol) in THF (5 mL), an aqueous lithium hydroxide solution (1 M, 2.3 mL, 2.3 mmol) was added at room temperature, and the resulting mixture was stirred at the same temperature for 2 hours. The mixture was neutralized by adding 1 M hydrochloric acid thereto, and then extracted with ethyl acetate. The organic layer was washed with saturated brine, dried over anhydrous magnesium sulfate, and then filtered and concentrated under reduced pressure to give H-341 as a yellow amorphous solid (194 mg, 0.443 mmol, 76%).

The measured NMR spectrum and HR-ESI-MS result of H-341 are described below.

$^1$H NMR (400 MHz, DMSOd$_6$) δ 3.18 (1H, dd, J=13.7, 7.3 Hz), 3.30 (1H, dd, J=13.7, 5.0 Hz), 4.63 (1H, ddd, J=7.8, 7.3, 5.0 Hz), 6.58-6.65 (3H, m), 7.38-7.70 (11H, m), 7.73 (1H, bs), 7.79-7.89 (3H, m), 9.20 (1H, bs); HRESIMS calcd for C$_{27}$H$_{22}$N$_2$O$_4$Na [M+Na]$^+$461.1477, found 461.1474.

The identified chemical structure of H-341 is indicated below.

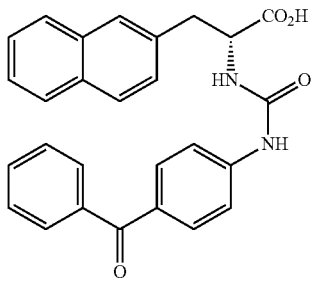 [SMILES: O=C(Nc1ccc(C(=O)c2ccccc2)cc1)N[C@H](Cc1ccc2ccccc2c1)C(=O)O]

H-341

(Example 1-25) Synthesis of H-521

To a solution of H-34 hydrochloride (200 mg, 0.753 mmol) and 9-carbazoleacetic acid (205 mg, 0.91 mmol) in DMF (2 mL), N-methylmorpholine (306 mg, 0.33 mL, 3.02 mmol) at room temperature and then 1-ethyl-3-(3-dimethylaminopropyl)carbodiimide hydrochloride (217 mg, 1.13 mmol) at the same temperature were added, and the resulting mixture was stirred at the same temperature for 1 day. Water was added to the mixture, and the resulting mixture was extracted with ethyl acetate. The organic layer was washed with saturated brine, dried over anhydrous magnesium sulfate, and then filtered and concentrated under reduced pressure. The residue was purified by silica gel column chromatography (hexane:ethyl acetate, 5:1 to 1:1) to give H-521 as a white powder (187 mg, 0.429 mmol, 57%).

The measured NMR spectrum and HR-ESI-MS result of H-521 are described below.

$^1$H NMR (400 MHz, CDCl$_3$) δ 2.96 (1H, dd, J=14.2, 7.4 Hz), 3.16 (1H, dd, J=14.2, 5.5 Hz), 3.63 (3H, s), 4.81 (1H, d, J=17.8 Hz), 4.88 (1H, d, J=17.8 Hz), 4.89-4.96 (1H, m), 5.95 (1H, d, J=8.2 Hz), 6.82 (1H, dd, J=8.3, 1.8 Hz), 7.12 (1H, bs), 7.16 (2H, d, J=7.8 Hz), 7.23 (2H, t, J=7.3 Hz), 7.32 (2H, t, J=7.3 Hz), 7.42-7.52 (4H, m), 7.71-7.76 (1H, m), 8.03 (2H, d, J=7.8 Hz); HRESIMS calcd for C$_{28}$H$_{24}$N$_2$O$_3$Na [M+Na]$^+$459.1685, found 459.1682.

The identified chemical structure of H-521 is indicated below.

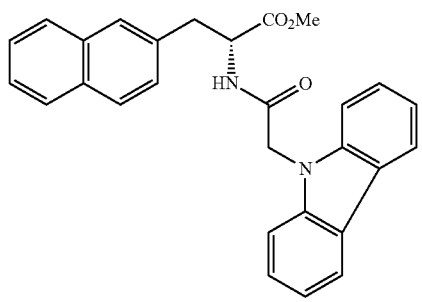 [SMILES: COC(=O)[C@@H](Cc1ccc2ccccc2c1)NC(=O)Cn1c2ccccc2c2ccccc21]

H-521

(Example 1-26) Synthesis of H-536

To a solution of H-521 (100 mg, 0.229 mmol) in THF (4 mL), an aqueous lithium hydroxide solution (1 M, 0.69 mL, 0.69 mmol) was added at room temperature, and the resulting mixture was stirred at the same temperature for 5 hours. The mixture was neutralized by adding 1 M hydrochloric acid thereto, and then extracted with ethyl acetate. The organic layer was washed with saturated brine, dried over anhydrous magnesium sulfate, and then filtered and concentrated under reduced pressure to give H-536 as a pale yellow crystal (85 mg, 0.201 mmol, 87%).

The measured NMR spectrum and HR-ESI-MS result of H-536 are described below.

$^1$H NMR (400 MHz, CDCl$_3$) δ 3.08 (1H, dd, J=13.7, 7.4 Hz), 3.26-3.32 (1H, m), 4.54-4.63 (1H, m), 4.92 (1H, d, J=16.9 Hz), 5.05 (1H, d, J=16.9 Hz), 7.11 (2H, td, J=7.3, 0.9 Hz), 7.16 (2H, td, J=6.8, 1.3 Hz), 7.24 (2H, d, J=7.8 Hz), 7.42 (1H, dd, J=8.7, 1.4 Hz), 7.48-7.55 (2H, m), 7.77 (1H, s), 7.82-7.87 (2H, m), 7.89-7.93 (1H, m), 8.07 (2H, d, J=7.3 Hz), 8.76 (1H, bs); HRESIMS calcd for C$_{27}$H$_{22}$N$_2$O$_3$Na [M+Na]$^+$445.1528, found 445.1525.

The identified chemical structure of H-536 is indicated below.

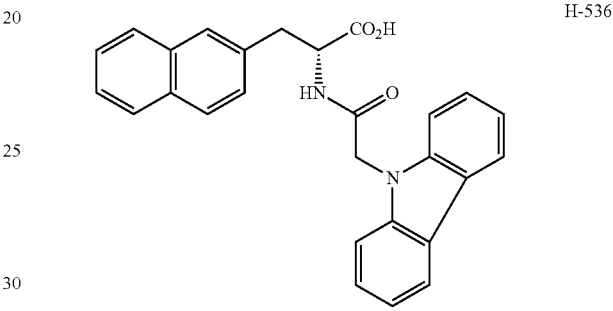

H-536

(Comparative Example 1-1) Synthesis of a Compound (H-65) as a Comparative Example A compound (H-65) was produced as an example for comparison with the compounds according to the present invention.

To a solution of D-naphthylalanine (200 mg, 0.93 mmol) in an aqueous sodium hydroxide solution (45 mg NaOH/0.5 mL), Z—Cl (239 mg, 0.20 mL, 1.4 mmol) at 0° C. and then an aqueous sodium hydroxide solution (45 mg NaOH/0.5 mL) at the same temperature were added, and the resulting mixture was stirred at the same temperature for 5 hours. After 1 M hydrochloric acid was added to the mixture, the resulting mixture was extracted with ethyl acetate. The organic layer was washed with saturated brine, dried over anhydrous magnesium sulfate, and then filtered and concentrated under reduced pressure. The residue was suspended in a mixture of ether and hexane, and the resulting suspension was filtered by suction, and the remaining solid was then washed with hexane to give H-65 as a white crystal (200 mg, 0.573 mmol, 62%).

The measured NMR spectrum and HR-ESI-MS result of H-65 are described below.

$^1$H NMR (400 MHz, DMSOd$_6$) δ 2.99 (1H, dd, J=14.2, 10.5 Hz), 3.23 (1H, dd, J=14.2, 4.6 Hz), 4.26-4.33 (1H, m), 4.93 (2H, s), 7.17-7.26 (5H, m), 7.41-7.51 (3H, m), 7.69-7.89 (5H, m), 7.45 (1H, dd, J=8.7, 1.9 Hz), 7.49-7.57 (2H, m), 7.75 (1H, d, J=7.3 Hz), 7.78-7.95 (5H, m), 8.81 (1H, d, J=8.2 Hz); HRESIMS calcd for C$_{21}$H$_{19}$NO$_4$Na [M+Na]$^+$ 372.1212, found 372.1212.

The identified chemical structure of H-65 is indicated below.

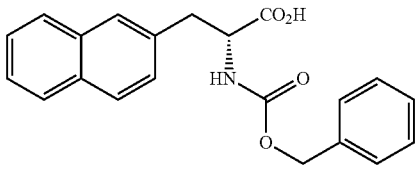
H-65

Example 2

(Evaluation of Pin1 Inhibition Activity)

To evaluate the inhibitory activity of each compound synthesized in Example 1 against the function of Pin1, a cell-based assay was performed according to the method previously developed by the inventors (Yusuke Nakatsu et al., Journal of Biological Chemistry, 2015, Vol. 290, No. 40, pp. 24255-24266), in which the phosphorylation level of AMPK (AMP-activated protein kinase), a protein whose phosphorylation is inhibited by Pin1, was examined as an index.

Briefly, 293T cells were plated on a collagen-coated 24-well plate. Forty-eight hours later, each compound synthesized in the preceding example (at 100 μM) was added to the plate, and the plate was left to stand in an incubator for 30 minutes. Subsequently, 10 mM 2-DG was added to the plate, and one hour later, each sample was collected with a buffer containing mercaptoethanol and SDS.

SDS-PAGE and blotting were performed, and blocking was then performed with 3% BSA for 1 hour, according to conventional protocols. Subsequently, a pAMPK antibody (Cell Signaling; diluted 1:2000 in Can Get Signal Solution 1, Toyobo) as a primary antibody, and an HRP-linked anti rabbit IgG (GE Healthcare; diluted 1:4000 in Can Get Signal Solution 2, Toyobo) as a secondary antibody were allowed to react at ambient temperature for 1 hour prior to detection.

The inhibitory activity against the function of Pin1 was evaluated by comparing the inhibition levels between each compound and a known Pin1 inhibitor, C1, as indicated below:

(+++): a higher level of AMPK phosphorylation is promoted, as compared with C1;
(++): a similar level of AMPK phosphorylation is promoted, as compared with C1;
(+): a lower level of AMPK phosphorylation is promoted, as compared with C1;
(−): no or almost no promotion is found in AMPK phosphorylation.

Some of the compounds synthesized in Example 1 were evaluated by the above-described method. The result is as follows:

(+++): H-103 (Example 1-7), H-109 (Example 1-9), H-178 (Example 1-20), H-334 (Example 1-22);
(++): H-101 (Example 1-5), H-161 (Example 1-11), H-158 (Example 1-13), H-162 (Example 1-15), H-163 (Example 1-17), H-341 (Example 1-24);
(+): H-62 (Example 1-3), H-164 (Example 1-19), H-521 (Example 1-25), H-536 (Example 1-26);
(−): H-105 (Example 1-8), H-65 (Comparative Example 1-1).

The activity was not measured in H-53, H-91, H-129, H-138, H-143, H-144, H-156, and H-291, which are esters formed by attachment of a methyl or benzyl group to the carboxylic acids of H-62, H-103, H-161, H-158, H-162, H-163, H-164, and H-341, respectively. These esters can be easily hydrolyzed into carboxylic acids, which are active compounds.

Additionally, the activity was not measured in H-85, which is an ester formed by attachment of a methyl group to the carboxylic acid of H-109. This ester can be easily hydrolyzed into a carboxylic acid, which is an active compound.

The result of the cell-based assay indicated that H-105 has no Pin1 inhibition activity, but H-105 is an ester formed by attachment of a benzyl group to the carboxylic acid of H-109. This ester can be easily hydrolyzed into a carboxylic acid, which is an active compound.

The results are summarized as shown in the following tables.

TABLE 1

| Example No. | Compound No. | Structural formula | Pin1 inhibition activity |
|---|---|---|---|
| Example 1-2 | H-53 | (naphthyl-CH₂-CH(NHC(O)-naphthyl-CO₂Me)-CO₂Bn) | Not measured (Hydrolysis causes conversion to H-62, which is active) |

TABLE 1-continued

| Example No. | Compound No. | Structural formula | Pin1 inhibition activity |
|---|---|---|---|
| Example 1-3 | H-62 | (naphthyl-CH₂-CH(CO₂H)-NH-C(=O)-naphthyl-CO₂Me) | + |
| Example 1-4 | H-85 | (naphthyl-CH₂-CH(CO₂Me)-NH-C(=O)-fluorenyl) | Not measured (Hydrolysis causes conversion to H-109, which is active) |
| Example 1-5 | H-101 | (naphthyl-CH₂-CH(CO₂H)-NH-C(=O)-C(OH)(fluorenyl)) | ++ |

TABLE 2

| Example No. | Compound No. | Structural formula | Pin1 inhibition activity |
|---|---|---|---|
| Example 1-6 | H-91 | (naphthyl-CH₂-CH(CO₂Me)-NH-C(=O)-CH₂-fluorenyl) | Not measured (Hydrolysis causes conversion to H-103, which is active) |

TABLE 2-continued

| Example No. | Compound No. | Structural formula | Pin1 inhibition activity |
|---|---|---|---|
| Example 1-7 | H-103 | | +++ |
| Example 1-8 | H-105 | | − |
| Example 1-9 | H-109 | | +++ |

TABLE 3

| Example No. | Compound No. | Structural formula | Pin1 inhibition activity |
|---|---|---|---|
| Example 1-10 | H-129 | | Not measured (Hydrolysis causes conversion to H-161, which is active) |
| Example 1-11 | H-161 | | ++ |

TABLE 3-continued

| Example No. | Compound No. | Structural formula | Pin1 inhibition activity |
|---|---|---|---|
| Example 1-12 | H-138 | 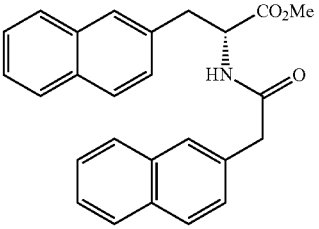 | Not measured (Hydrolysis causes conversion to H-158, which is active) |
| Example 1-13 | H-158 | 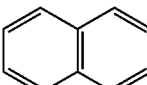 | ++ |

TABLE 4

| Example No. | Compound No. | Structural formula | Pin1 inhibition activity |
|---|---|---|---|
| Example 1-14 | H-143 | 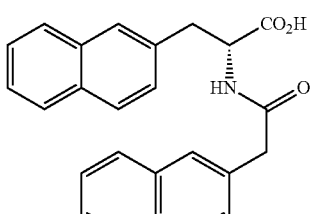 | Not measured (Hydrolysis causes conversion to H-162, which is active) |
| Example 1-15 | H-162 | 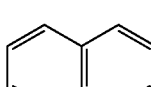 | ++ |
| Example 1-16 | H-144 | 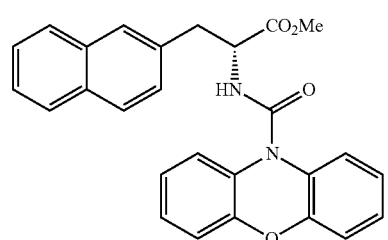 | Not measured (Hydrolysis causes conversion to H-163, which is active) |

TABLE 4-continued

| Example No. | Compound No. | Structural formula | Pin1 inhibition activity |
|---|---|---|---|
| Example 1-17 | H-163 | (naphthyl-CH2-CH(CO2H)-NH-C(O)-N(carbazole)) | ++ |

TABLE 5

| Example No. | Compound No. | Structural formula | Pin1 inhibition activity |
|---|---|---|---|
| Example 1-18 | H-156 | (naphthyl-CH2-CH(CO2Me)-NH-C(O)-N(dibenzazepine)) | Not measured (Hydrolysis causes conversion to H-164, which is active) |
| Example 1-19 | H-164 | (naphthyl-CH2-CH(CO2H)-NH-C(O)-N(dibenzazepine)) | + |
| Example 1-20 | H-178 | (naphthyl-CH2-CH(CO2H)-NH-C(O)-N(dihydrodibenzazepine)) | +++ |
| Example 1-21 | H-287 | (naphthyl-CH2-CH(CO2Me)-NH-C(O)-NH-(2-phenoxyphenyl)) | Not measured (Hydrolysis causes conversion to H-334, which is active) |

TABLE 6

| Example No. | Compound No. | Structural formula | Pin1 inhibition activity |
|---|---|---|---|
| Example 1-22 | H-334 | (naphthalene-CH2-CH(CO2H)-NH-C(=O)-NH-phenyl-O-phenyl) | +++ |
| Example 1-23 | H-291 | (naphthalene-CH2-CH(CO2Me)-NH-C(=O)-NH-phenyl-C(=O)-phenyl) | Not measured (Hydrolysis causes conversion to H-341, which is active) |
| Example 1-24 | H-341 | (naphthalene-CH2-CH(CO2H)-NH-C(=O)-NH-phenyl-C(=O)-phenyl) | ++ |
| Example 1-25 | H-521 | (naphthalene-CH2-CH(CO2Me)-NH-C(=O)-CH2-carbazole) | + |

TABLE 7

| Example No. | Compound No. | Structural formula | Pin1 inhibition activity |
|---|---|---|---|
| Example 1-26 | H-536 | 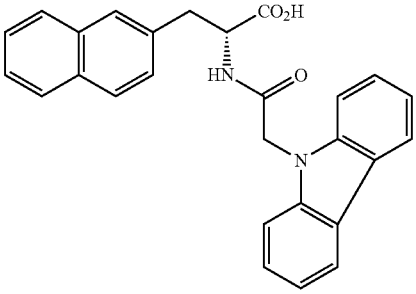 [SMILES: O=C(Cn1c2ccccc2c2ccccc21)N[C@H](Cc1ccc2ccccc2c1)C(=O)O] | + |
| Comparative Example 1-1 | H-65 | 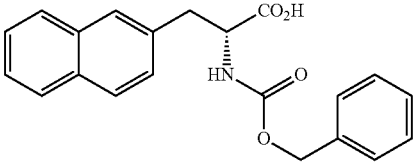 [SMILES: O=C(N[C@H](Cc1ccc2ccccc2c1)C(=O)O)OCc1ccccc1] | − |

Example 3

(NASH Treatment Study)

Example 3-1

Animal experiments were performed using non-alcoholic steatohepatitis (NASH) model mice to test the compounds according to the present invention for the therapeutic effect on NASH.

NASH model mice (hereinafter referred to as "NASH mice") were produced by feeding a high-fat diet containing trans fatty acids (HFDT) to individual male laboratory mice (C57BL/6J) for 8 weeks. The mice were divided into groups, and animal experiments were performed on a group of mice to which a compound according to the present invention (H-163 or H-144) was administered intraperitoneally at a dose of 2.5 mg/kg/day three times a week, a group of mice to which a compound according to the present invention (H-163 or H-144) was administered orally at a dose of 5.0 mg/kg/day three times a week, a group of mice to which Juglone, a known Pin1 inhibitor, was administered intraperitoneally at a dose of 2.5 mg/kg/day three times a week, a group of mice to which Juglone was administered orally at a dose of 5.0 mg/kg/day three times a week, and a group of mice to which nothing was administered, during the 8-week HFDT feeding period. In addition, a normal diet was given to individual male laboratory mice ($C_{57}BL/6J$) for 8 weeks to prepare control mice.

The results of measurements of liver weight change, blood ALT (GPT) concentration, and fasting blood glucose in these mice are separately shown in FIGS. 1 (A) to (C).

FIG. 1 (A) is a graph depicting the result of measurement of mouse liver weight, and graph bars represent the results of measurement of liver weight in the control mice, the NASH mice, the NASH mice treated by intraperitoneal administration of H-163, the NASH mice treated by oral administration of H-163, the NASH mice treated by intraperitoneal administration of H-144, the NASH mice treated by oral administration of H-144, the NASH mice treated by intraperitoneal administration of Juglone, and the NASH mice treated by oral administration of Juglone, from left to right.

As shown in FIG. 1 (A), the liver weight was increased in the NASH mice as a result of fat accumulation in the liver. In contrast, the increase in liver weight was significantly reduced when either of the compounds according to the present invention (H-163 and H-144) was administered. Additionally, the increase in liver weight was significantly reduced in the NASH mice treated by oral administration of Juglone, while the NASH mice treated by intraperitoneal administration of Juglone were all dead within 8 weeks. Severe side effects were suspected to have occurred because of the low specificity of Juglone as a Pin1 inhibitor.

FIG. 1 (B) is a graph depicting the result of measurement of blood ALT (GPT) concentration (IU/ml), and graph bars represent the results of measurement of blood ALT in the control mice, the NASH mice, the NASH mice treated by intraperitoneal administration of H-163, the NASH mice treated by oral administration of H-163, the NASH mice treated by intraperitoneal administration of H-144, the NASH mice treated by oral administration of H-144, the NASH mice treated by intraperitoneal administration of Juglone, and the NASH mice treated by oral administration of Juglone, from left to right.

As shown in FIG. 1 (B), the ALT value, an index of liver inflammation, was increased in the NASH mice given no Pin1 inhibitor. In contrast, the ALT value was decreased and inhibition of liver inflammation was observed when either of the compounds according to the present invention (H-163 and H-144) was administered.

FIG. 1 (C) is a graph depicting the result of measurement of fasting blood glucose concentration (mg/dl), and graph bars represent the results of measurement of fasting blood glucose level in the control mice, the NASH mice, the NASH mice treated by intraperitoneal administration of H-163, the NASH mice treated by oral administration of H-163, the NASH mice treated by intraperitoneal administration of H-144, the NASH mice treated by oral administration of H-144, the NASH mice treated by intraperitoneal administration of Juglone, and the NASH mice treated by oral administration of Juglone, from left to right.

As shown in FIG. 1 (C), the NASH mice treated by intraperitoneal administration of Juglone were all dead within 8 weeks, and the NASH mice treated by oral administration of Juglone were not dead but showed an abnormal increase in blood glucose level. In contrast, no significant abnormality in fasting blood glucose level was detected in the NASH mice given either of the compounds according to the present invention (H-163 and H-144). Juglone is a less specific Pin1 inhibitor and causes severe side effects. In this respect, the compounds according to the present invention were confirmed to have significantly decreased side effects.

Example 3-2

Figure 2:
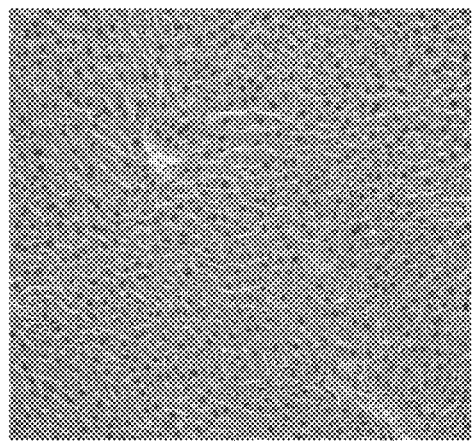
FIG. 2 shows photographs provided instead of drawings and depicting results of microscopic observation of liver tissue sections from mice in a NASH treatment study.
Figure 2:
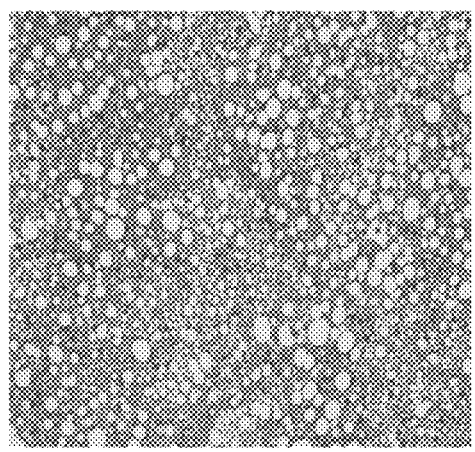
Figure 2:
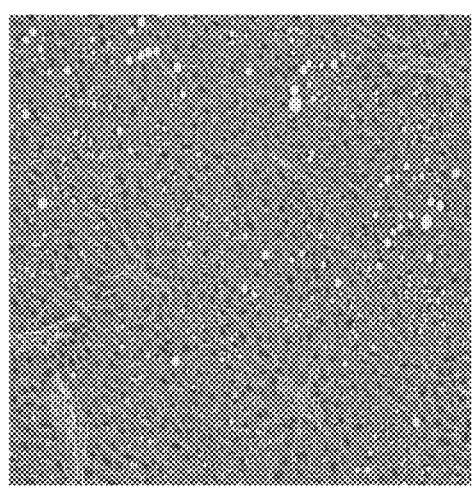

FIG. 2 shows results of microscopic observation of liver tissue sections from the control mice given a normal diet, the NASH mice given a HFDT, and the NASH mice given a HFDT and H-163.

FIG. 2 (A) is a photograph depicting the result of observation of liver tissue from the control mice given a normal diet, and FIG. 2 (B) is a photograph depicting the result of observation of liver tissue from the NASH mice given a HFDT, and FIG. 2 (C) is a photograph depicting the result of observation of liver tissue from the NASH mice given a HFDT and H-163.

No fat accumulation was observed in the liver tissue from the control mice, as shown in FIG. 2 (A), while an accumulation of fat was found in the liver tissue from the NASH mice given a HFDT, as shown in FIG. 2 (B). However, administration of H-163 significantly reduced fat accumulation even in the NASH mice, as shown in FIG. 2 (C).

Example 3-3

Next, an animal experiment was performed on NASH mice that were produced by feeding a methionine-choline-deficient diet (MCDD).

NASH mice were produced by feeding a methionine-choline-deficient diet (MCDD) to individual male laboratory mice (C57BL/6J) for 8 weeks. The mice were divided into groups, and an animal experiment was performed on a group of mice to which a compound according to the present invention (H-163) was administered intraperitoneally at a dose of 2.5 mg/kg/day three times a week, and a group of mice to which nothing was administered, during the 8-week MCDD feeding period. In addition, a normal diet was given to individual male laboratory mice (C57BL/6J) for 8 weeks to prepare control mice.

Figure 3:
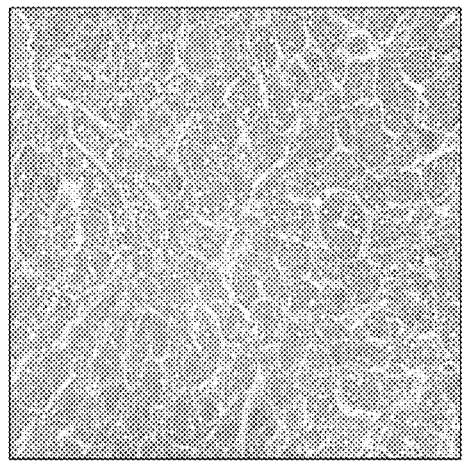
FIG. 3 shows photographs provided instead of drawings and depicting results of microscopic observation of liver tissue sections with Azan staining from mice in a NASH treatment study.
Figure 3:
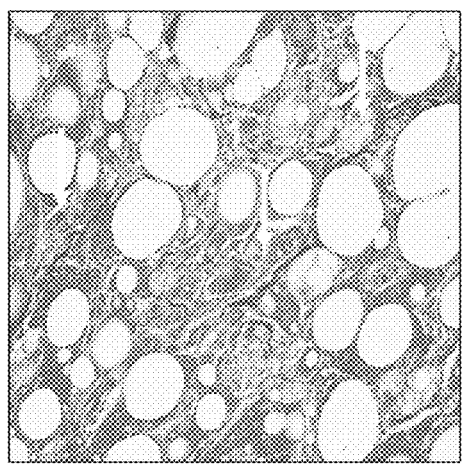
Figure 3:
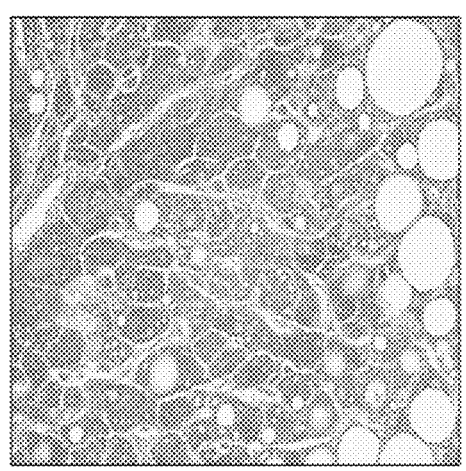

FIG. 3 shows results of microscopic observation of liver tissue sections with Azan staining from those mice.

FIG. 3 (A) is a photograph depicting the result of observation of liver tissue from the control mice, and FIG. 3 (B) is a photograph depicting the result of observation of liver tissue from the NASH mice given a MCDD, and FIG. 3 (C) is a photograph depicting the result of observation of liver tissue from the NASH mice given a MCDD and H-163.

No fat accumulation was observed in the liver tissue from the control mice, as shown in FIG. 3 (A), while an accumulation of fat was found in the liver tissue from the NASH mice given a MCDD, as shown in FIG. 3 (B). In addition, administration of H-163 significantly reduced fat accumulation even in the NASH mice, as shown in FIG. 3 (C). Moreover, as shown in FIG. 3 (B), fibrosis (the colored area pointed by a white arrow) was observed in the liver tissue with Azan staining, in the case where H-163 was not administered. In contrast, as shown in FIG. 3 (C), hepatic fibrosis was significantly inhibited when H-163 was administered.

Example 4

(Cancer Treatment Study)

Example 4-1

An animal experiment was performed using mice transplanted with cancer cells to test the therapeutic effects of the compounds according to the present invention on cancer.

A first tumor (DU145 cells) with Matrigel plug was implanted in the middle of the upper back of nude mice (BALB/c-slc-nu/nu mice).

Five weeks after the first implantation, a second tumor (DU145 cells) was implanted in the middle of the left and right sides of the back of the nude mice.

Intraperitoneal administration of a compound according to the present invention, H-163 or H-144, at a dose of 2.5 mg/kg/day and a frequency of 5 times a week was started 6 weeks after the first implantation, at which the first tumor became measurable (at this timing, the second tumor was so small in size and not measurable), and was continued for 9 weeks. No compound was administered to a group of mice to prepare control mice.

Figure 4:
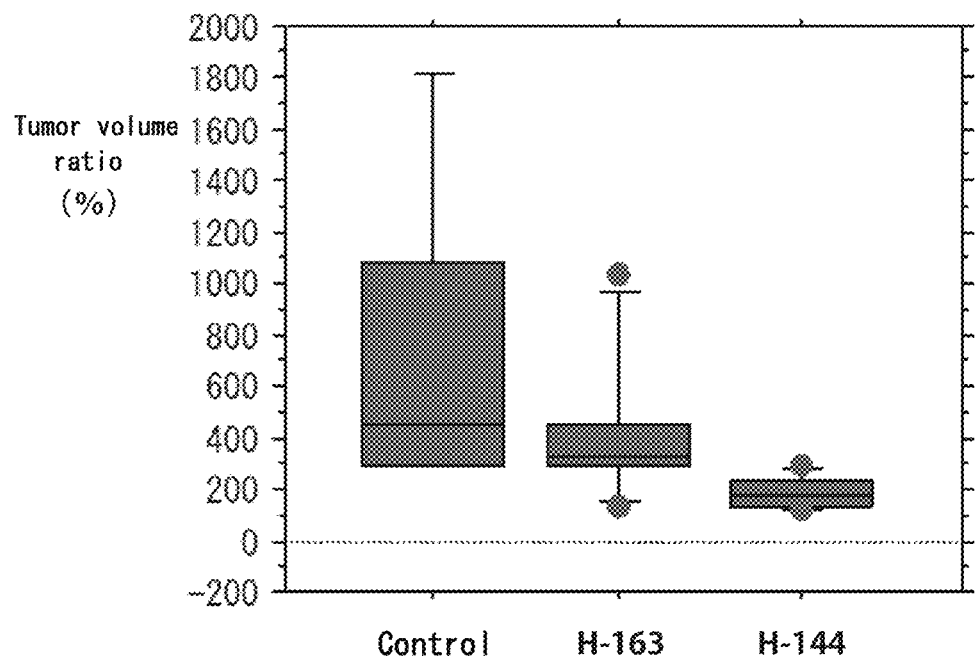
FIG. 4 shows graphs depicting results of measurement of volume change in a first tumor and a second tumor from mice in a cancer treatment study.
Figure 4:
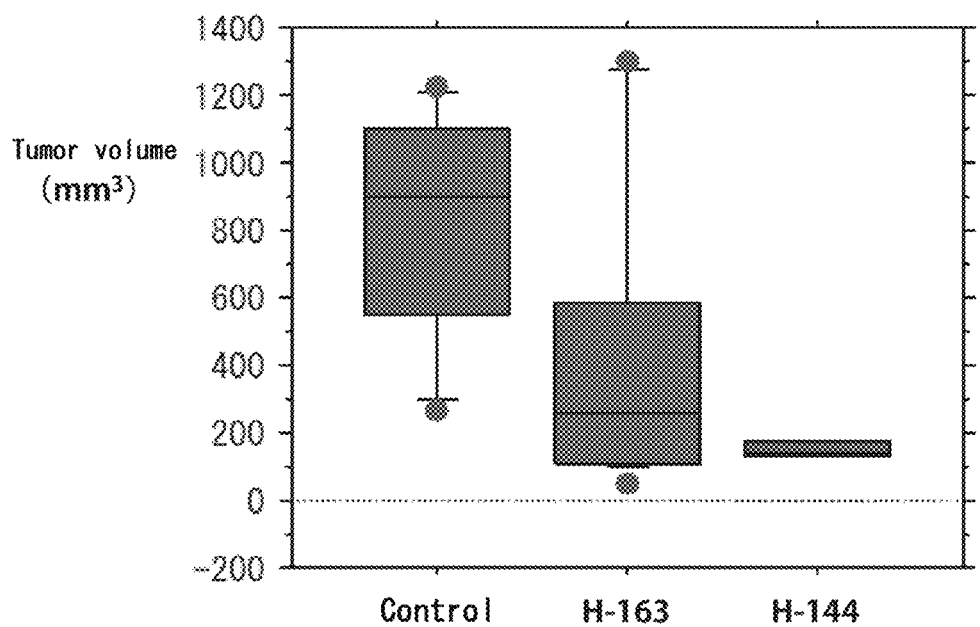

FIG. 4 shows results of measurement of volume change in the first tumor and the second tumor at 9 weeks after the initial administration. FIG. 4 (A) illustrates the distribution of tumor volume ratio (%) in the first tumor at 9 weeks after administration of each compound, where the tumor volume at the beginning of the administration is set as 100, and shows the distribution of size change in the control mice, the mice given H-163, and the mice given H-144, from left to right, expressed in box plot.

As shown in FIG. 4 (A), tumor size growth was suppressed in the mice given H-163 or H-144 compared to that in the control mice.

FIG. 4 (B) illustrates the distribution of volume of the second tumor and shows the distribution of tumor volume in the control mice, the mice given H-163, and the mice given H-144, from left to right, expressed in box plot. The volume of the second tumor was so small and not measurable at the beginning of administration of each compound. Therefore, the result from the second tumor is expressed in volume ($mm^3$), but not in ratio.

As shown in FIG. 4 (B), tumor size growth was suppressed in the mice given H-163 or H-144 compared to that in the control mice.

Example 4-2

Colon cancer model mice were produced by intraperitoneal administration of azoxymethane (AOM) at a dose of 12 mg/kg to laboratory mice on Day 1, and then starting a course consisting of 5-day oral administration of 3% sodium dextran sulfate (DSS) and 16-day no DSS administration, on Day 6, and repeating the course 4 times, to induce colon inflammation and subsequent cancer development. The mice were divided into a group of mice to which a compound according to the present invention (H-163) was administered and a group of mice (control) to which none of the compounds according to the present invention was administered, and the compound according to the present invention (H-163) was administered orally to the former mice at a dose of 1.25 mg/kg/day and a frequency of three times a week from Day 6 until the last day of the experiment.

On Day 89, the colon cancer model mice were dissected to count the number of developed colon cancer tissues and to measure tumor area occupied by a single colon cancer tissue (total tumor area/tumor tissue number).

Figure 5:
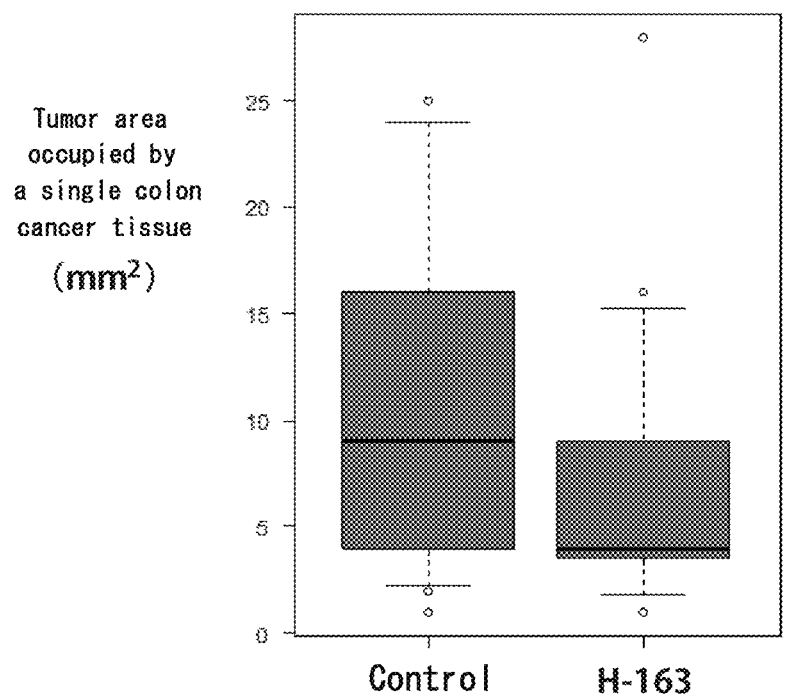
FIG. 5 shows a graph depicting a result of measurement of tumor area occupied by a single colon cancer tissue in a treatment study using colon cancer model mice. The distribution of tumor area in colon cancer model mice (control) administered with none of compounds according to the present invention and in colon cancer model mice administered with H-163, from left to right, is illustrated by box plot.

FIG. 5 shows a graph depicting the distribution of tumor area occupied by a single colon cancer tissue in individual mice, and illustrates the distribution of tumor area in the colon cancer model mice (control) administered with none of the compounds according to the present invention and in the colon cancer model mice administered with H-163, from left to right, expressed in box plot.

Colon cancer developed in both the groups and no significant difference in number of colon cancer tissues was found between both the groups. However, as shown in FIG. 5, a reduction in tumor area was observed in the colon cancer model mice given H-163 compared to the control colon cancer model mice, and particularly a significant difference in median value was found between the groups.

INDUSTRIAL APPLICABILITY

The compounds or salts thereof, Pin1 inhibitors, pharmaceutical compositions, therapeutic or prophylactic agents for inflammatory diseases associated with fibrosis, for cancer, and for obesity according to the present invention are each useful in the pharmaceutical industry.

The invention claimed is:

1. A compound represented by Formula (I), or a salt thereof:

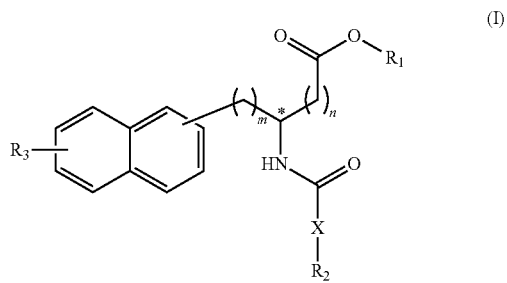

(I)

wherein m represents an integer of 0 to 2, and n represents an integer of 0 to 1, provided that $0 \leq m+n \leq 2$;

$R_1$ represents a hydrogen atom, an optionally substituted hydrocarbon group, an optionally substituted heterocyclic group, or an optionally substituted amino group;

$R_2$ represents an optionally substituted fluorenyl group, a substituted naphthyl group, or an optionally substituted group represented by any one of the following structures:

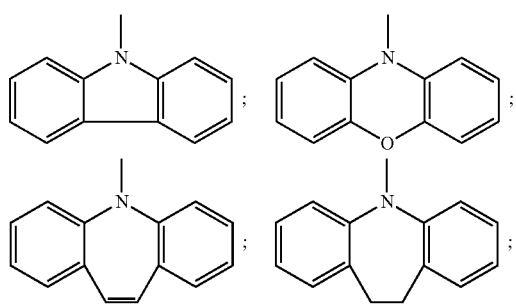

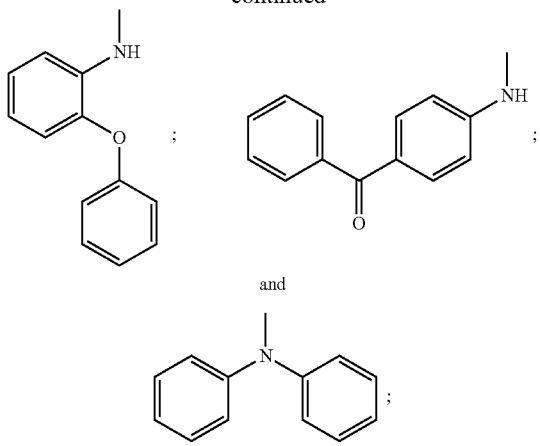

$R_3$ represents 0 to 7 identical or different substituents attached to the naphthyl group; and X represents a single bond, —$CH_2$— group, or —NH— group.

2. The compound or a salt thereof according to claim 1, wherein m is 1 and n is 0.

3. The compound or a salt thereof according to claim 1, wherein $R_1$ represents a hydrogen atom.

4. The compound or a salt thereof according to claim 1, wherein X represents a single bond.

5. A Pin1 inhibitor comprising a compound represented by Formula (I) or a salt thereof:

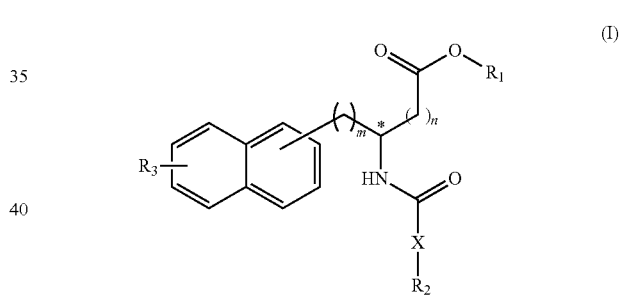

(I)

wherein m represents an integer of 0 to 2, and n represents an integer of 0 to 1, provided that $0 \leq m+n \leq 2$;

$R_1$ represents a hydrogen atom, an optionally substituted hydrocarbon group, an optionally substituted heterocyclic group, or an optionally substituted amino group;

$R_2$ represents an optionally substituted fluorenyl group, a substituted naphthyl group, or an optionally substituted group represented by any one of the following structures:

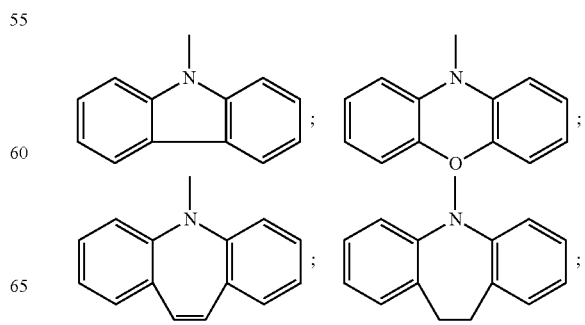

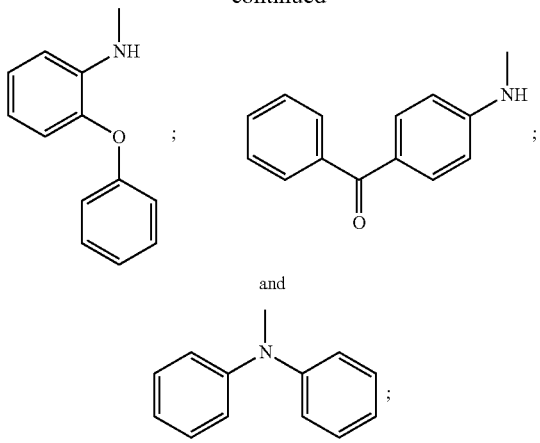

and

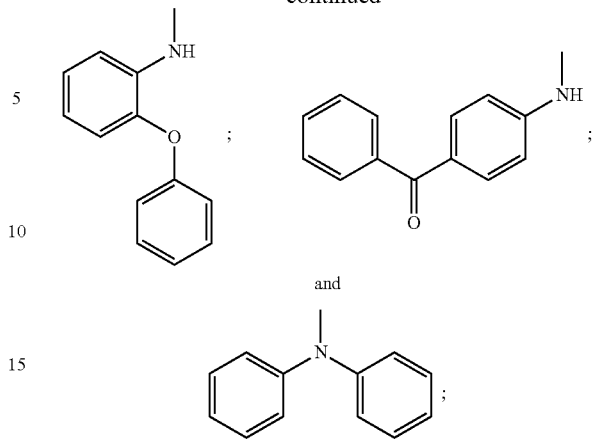

and

R₃ represents 0 to 7 identical or different substituents attached to the naphthyl group; and X represents a single bond, —CH₂— group, or —NH— group.

6. A pharmaceutical composition comprising the compound or a pharmaceutically acceptable salt thereof according to claim 1 and a pharmaceutically acceptable carrier.

7. A therapeutic agent for the treatment of an inflammatory disease associated with fibrosis, comprising a compound represented by Formula (I) or a pharmaceutically acceptable salt thereof as an active ingredient:

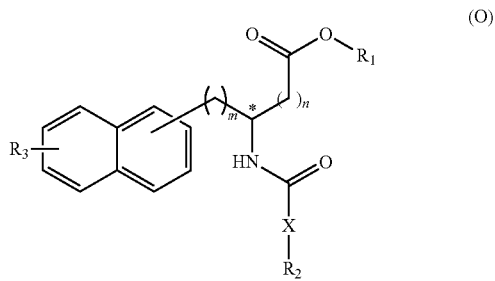

(O)

wherein m represents an integer of 0 to 2, and n represents an integer of 0 to 1, provided that 0≤m+n≤2;

R₁ represents a hydrogen atom, an optionally substituted hydrocarbon group, an optionally substituted heterocyclic group, or an optionally substituted amino group;

R₂ represents an optionally substituted fluorenyl group, a substituted naphthyl group, or an optionally substituted group represented by any one of the following structures:

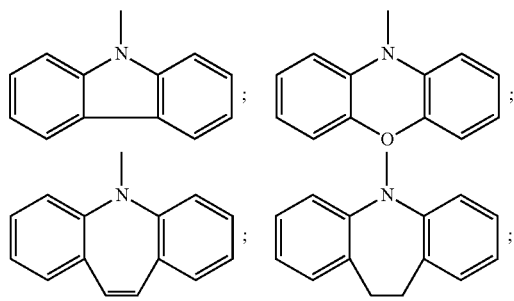

R₃ represents 0 to 7 identical or different substituents attached to the naphthyl group; and X represents a single bond, —CH₂— group, or —NH— group.

8. The therapeutic agent according to claim 7, further comprising an active ingredient of at least one additional drug for the treatment of the inflammatory disease associated with fibrosis.

9. A method of treating an inflammatory disease associated with fibrosis, comprising administering the therapeutic agent according to claim 7, in combination with at least one additional drug for the treatment of the inflammatory disease associated with fibrosis.

10. A method of preparing a medicament for the treatment of an inflammatory disease associated with fibrosis, comprising combining a pharmaceutically acceptable carrier and a therapeutic amount of the compound or a pharmaceutically acceptable salt thereof according to claim 1.

11. A method of treating an inflammatory disease associated with fibrosis, comprising administering the compound or a pharmaceutically acceptable salt thereof according to claim 1 to a patient in need thereof.

12. A therapeutic agent for the treatment of cancer, comprising a compound represented by Formula (I) or a pharmaceutically acceptable salt thereof as an active ingredient:

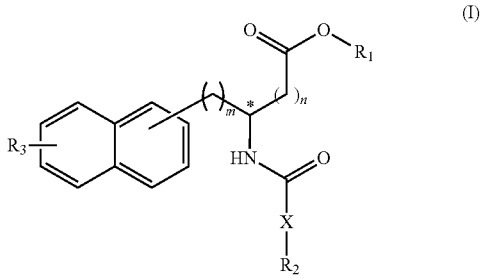

(I)

wherein m represents an integer of 0 to 2, and n represents an integer of 0 to 1, provided that 0≤m+n≤2;

R₁ represents a hydrogen atom, an optionally substituted hydrocarbon group, an optionally substituted heterocyclic group, or an optionally substituted amino group;

R₂ represents an optionally substituted fluorenyl group, a substituted naphthyl group, or an optionally substituted group represented by any one of the following structures:

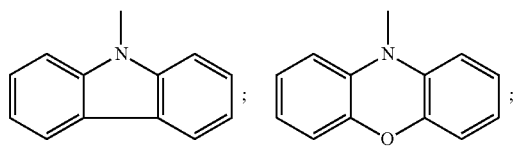

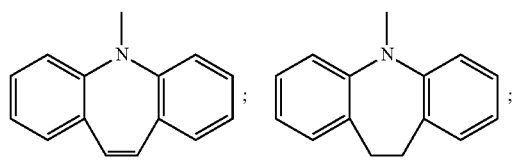

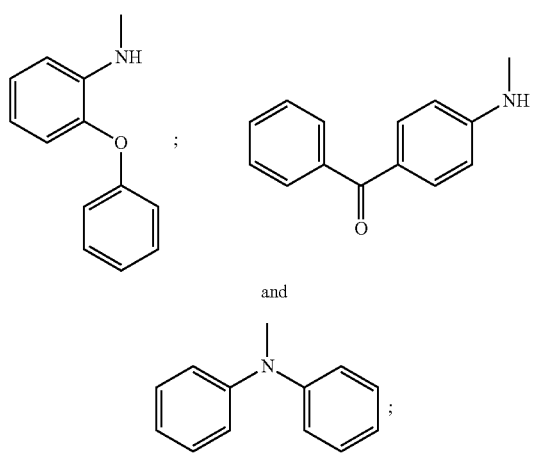

and

R₃ represents 0 to 7 identical or different substituents attached to the naphthyl group; and X represents a single bond, —CH₂— group, or —NH— group.

13. The therapeutic agent according to claim 12, wherein the cancer is colon cancer or prostate cancer.

14. The therapeutic agent according to claim 12, further comprising an active ingredient of at least one additional drug for the treatment of cancer.

15. A method of treating cancer, comprising administering the therapeutic agent according to claim 12, in combination with at least one additional drug for the treatment of cancer.

16. A method of preparing a medicament for the treatment of cancer, comprising combining a pharmaceutically acceptable carrier and a therapeutic amount of the compound or a pharmaceutically acceptable salt thereof according to claim 1.

17. A method of treating cancer, comprising administering the compound or a pharmaceutically acceptable salt thereof according to claim 1 to a patient in need thereof.

18. A therapeutic agent for the treatment of obesity, comprising a compound represented by Formula (I) or a pharmaceutically acceptable salt thereof as an active ingredient:

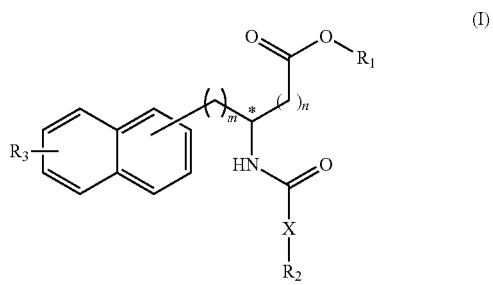

wherein m represents an integer of 0 to 2, and n represents an integer of 0 to 1, provided that 0≤m+n≤2;

R₁ represents a hydrogen atom, an optionally substituted hydrocarbon group, an optionally substituted heterocyclic group, or an optionally substituted amino group;

R₂ represents an optionally substituted fluorenyl group, a substituted naphthyl group, or an optionally substituted group represented by any one of the following structures:

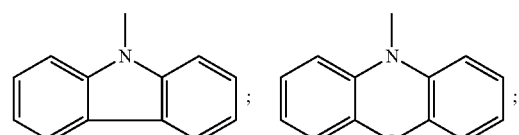

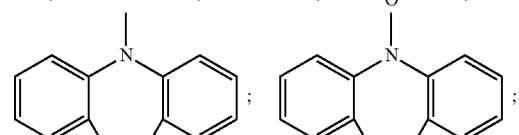

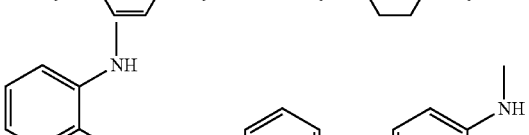

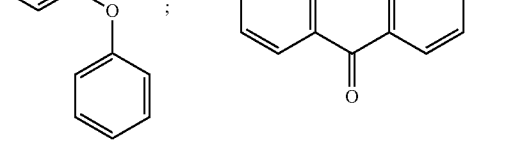

and

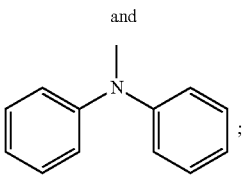

R₃ represents 0 to 7 identical or different substituents attached to the naphthyl group; and X represents a single bond, —CH₂— group, or —NH— group.

19. The therapeutic agent according to claim 18, further comprising an active ingredient of at least one additional drug for the treatment of obesity.

20. A method of treating obesity, comprising administering the therapeutic agent according to claim 18, in combination with at least one additional drug for the treatment of obesity.

21. A method of preparing a medicament for the treatment of obesity, comprising combining a pharmaceutically acceptable carrier and a therapeutic amount of the compound or a pharmaceutically acceptable salt thereof according to claim 1.

22. A method of treating obesity, comprising administering the compound or a pharmaceutically acceptable salt thereof according to claim 1 to a patient in need thereof.

\* \* \* \* \*